(12) United States Patent
Sun

(10) Patent No.: US 10,717,762 B2
(45) Date of Patent: Jul. 21, 2020

(54) ABIRATERONE DERIVATIVE AND FORMULATIONS THEREOF

(71) Applicants:Zhuhai Beihai Biotech Co., Ltd., Jinwan, Zhuhai (CN); Qun Sun, Princeton, NJ (US)

(72) Inventor: Qun Sun, Princeton, NJ (US)

(73) Assignee: Zhuhai Beihai Biotech Co., Ltd.

( * ) Notice: Subject to any disclaimer, the term of this patent is extended or adjusted under 35 U.S.C. 154(b) by 0 days.

(21) Appl. No.: 16/341,206

(22) PCT Filed: Oct. 11, 2017

(86) PCT No.: PCT/US2017/056142
§ 371 (c)(1),
(2) Date: Apr. 11, 2019

(87) PCT Pub. No.: WO2018/071544
PCT Pub. Date: Apr. 19, 2018

(65) Prior Publication Data
US 2019/0315797 A1 Oct. 17, 2019

Related U.S. Application Data

(60) Provisional application No. 62/406,701, filed on Oct. 11, 2016.

(51) Int. Cl.
*C07J 43/00* (2006.01)
*A61K 47/64* (2017.01)
*A61K 9/08* (2006.01)

(52) U.S. Cl.
CPC .............. *C07J 43/003* (2013.01); *A61K 9/08* (2013.01); *A61K 47/643* (2017.08)

(58) Field of Classification Search
CPC ......... C07J 43/003; A61K 47/643; A61K 9/08
USPC ....................................................... 546/342
See application file for complete search history.

(56) References Cited

U.S. PATENT DOCUMENTS

| | | |
|---|---|---|
| 5,604,213 A | 2/1997 | Bathe et al. |
| 8,076,474 B2 | 12/2011 | Hunt |
| 8,338,588 B2 | 12/2012 | Hunt |
| 2014/0256932 A1 | 9/2014 | Derrien et al. |
| 2016/0083416 A1 | 3/2016 | Poirier et al. |
| 2016/0237109 A1 | 8/2016 | Cheng et al. |

OTHER PUBLICATIONS

Mariya Sokol et al. Developement of novel PLGA nanoparticles with encapsulations of docetaxel and Aberaterone acetate for a highly efficient delivery into tumor cells. (Year: 2018).*
Bosse et al., "Phase I Comparability of Recombinant Human Albumin and Human Serum Albumin", J Clin. Pharmacol., 45: 57-67, 2005.
Carter et al., "Structure of Serum Albumin", Adv. Protein. Chem., 45, 153-203, 1994.
Chen et al., "Human serum albumin from recombinant DNA technology: Challenges and strategies", Biochimica et Biophysica Acta., 1830: 5515-5525, 2013.
Chen, "Removal of Fatty Acids from Serum Albumin by Charcoal Treatment", J Biol. Chem., 242: 173-181, 1967.
Cohn et al., "Preparation and Properties of Serum and Plasma Proteins. IV. A System for the Separation into Fractions of the Protein and Lipoprotein Components of Biological Tissues and Fluids", J Am. Chem. Soc., 68: 459-475, 1946.
Curry et al., "Crystal structure of human serum albumin complexed with fatty acid reveals an asymmetric distribution of binding sites", Nat. Struct. Biol., 5, 827-35, 1998.
Fehske et al., "The location of drug binding sites in human serum albumin", Biochem. Pharmcol., 30, 687-92, 1981.
Finlayson, "Albumin Products", Seminars in Thrombosis and Hemostasis, 6, 85-120, 1980.
Goodman et al., The Pharmacological Basis of Therapeutics, 9th ed, JVlcGraw-Hill New York, 1996.
Hauser et al., "Oxygen transport responses to colloids and crystalloids in critically ill surgical patients.", Surgery, Gynecology and Obstetrics, 150, 811-816, 1980.
He et al. "Atomic structure and chemistry of human serum albumin", Nature, 358, 209-15, 1992.
International Preliminary Report on Patentability in App. No. PCT/US2017/056142, dated Apr. 16, 2019, 5 pages.
Kasim et al.,"Molecular Properties of WHO Essential Drugs and Provisional Biopharmaceutical Classification," Molecular Pharmaceutics, 1 (1): p. 85-96, 2004.
Kragh-Hansen, "Structure and ligand binding properties of human serum albumin", Dan. Aled Bull., 1441, 131-40, 1990.
Lee et al., "An intravenous formulation decision tree for discovery compound formulation development", International Journal of Pharmaceutics 253, 111-119, 2003.
Lin et al., "Stability of Human Serum Albumin During Bioprocessing: Denaturation and Aggregation During Processing of Albumin Paste", Pharmaceutical Research, 17:391-6, 2000.
Lipinski, "Drug-like properties and the causes of poor solubility and poor permeability.", Journal of Pharmacological and Toxicological Methods, 44(1): p. 235-249, 2000.

(Continued)

*Primary Examiner* — Rita J Desai
(74) *Attorney, Agent, or Firm* — Fish & Richardson P.C.

(57) ABSTRACT

This document relates to an abiraterone derivative, 2-(((3S, 8R,9S,10R,13S,14S)-10,13-dimethyl-17-(pyridin-3-yl)-2,3, 4,7,8,9,10,11,12,13,14,15-dodecahydro-1H-cyclopenta[a] phenanthren-3-yl)oxy)-2-oxoacetic acid (ABOA). This document also relates to compositions comprising a non-covalently bound complex comprising ABOA and human serum albumin, wherein the ABOA and the human serum albumin in the composition have a ratio of weight from about 1:1 to about 1:2000. This document also relates to compositions comprising ABOA and human serum albumin, wherein the ABOA and the human serum albumin in the composition have a ratio of weight from about 1:1 to about 1:2000. This document also relates to compositions consisting essentially of ABOA and human serum albumin, wherein the ABOA and the human serum albumin in the composition have a ratio of weight from about 1:1 to about 1:2000.

14 Claims, No Drawings

(56) References Cited

OTHER PUBLICATIONS

Ratain, "Flushing oral oncology drugs down the toilet," Clinical Oncology, 29(30): 3958-3959, 2011.
Sartor et al., "Novel Therapeutic Strategies for Metastatic Prostate Cancer in the Post-Docetaxel Setting", The Oncologist, 16: 1487-1497, 2011.
Sugio et al. "Crystal structure of human serum albumin at 2.5 Å resolution", Protein. Eng., 12, 439-46, 1999.
Tullis, "Albumin", JAAIA, 237, 355-360, 460-463, 1977.
Vorum, "Reversible ligand binding to human serum albumin. Theoretical and clinical aspects.", Dan. Med. Bull., 46, 379-99, 1999.
International Search Report and Written Opinion for App. No. PCT/US2017/056142, dated Dec. 15, 2017, 12 pages.

\* cited by examiner

ABIRATERONE DERIVATIVE AND FORMULATIONS THEREOF

CLAIM OF PRIORITY

This application claims the benefit of U.S. provisional application No. 62/406,701 filed Oct. 11, 2016. The entire content of the foregoing is hereby incorporated by reference.

TECHNICAL FIELD

This document relates to compositions and formulations for the treatment of proliferative diseases, and more particularly to compositions and formulations comprising abiraterone derivative.

BACKGROUND

About 30% of drugs that appear on the World Health Organization (WHO) Essential Drug List were reported to be poorly water-soluble, based on the Biopharmaceutics Classification System (BCS). See, for example, Kasim, N. A., et al., Molecular properties of WHO essential drugs and provisional biopharmaceutical classification, *Molecular Pharmaceutics* 2004, 1(1): p. 85-96. Over 40% of newly developed pharmaceutically active substances have solubility issues (Lipinski, C. A., Drug-like properties and the causes of poor solubility and poor permeability, *Journal of Pharmacological and Toxicological Methods* 2000, 44(1): p. 235-249). The poor dissolution and/or permeability of these drugs often result in low and highly variable bioavailability. A major obstacle of successfully commercializing these compounds is the difficulty of enhancing their dissolution rate and extent of dissolution.

For example, abiraterone acetate is approved in the United States as an oral treatment for metastatic castration-resistant prostate cancer. The product insert describes abiraterone acetate as a lipophilic compound that is practically insoluble in water (Zytiga™ Full Prescribing Information, 2012, Janssen Biotech Inc., Section 11). While the insolubility of abiraterone acetate allows for its preparation in capsule form for oral dosing, it precludes intravenous (IV) administration which is used for other treatments for prostate cancer, such as Cabazitaxel (Sartor, O. et al. *The Oncologist* 2011, 16: 1487-1497).

Due to its insolubility, abiraterone acetate suffers from low bioavailability that arises from poor absorption, as 77% of the administered drug is excreted (Ratain, M. J. *Journal of Clinical Oncology* 2011, 29(30): 3958-3959). Thus, most of the administered drug is not used for its intended treatment.

The low water solubility of abiraterone acetate has led a food-effect greater than any other marketed drug (five- to ten-fold, depending on fat content of the meal), and a significant interindividual pharmacokinetic variability. This food-effect can also afford a large intraindividual variability, resulting in underdosing or overdosing. Strict patient compliance is thus required to achieve the dosing under labeled conditions.

Further, abiraterone acetate is a substrate of the CYP3A4 liver enzyme, which can lead to potential drug-drug interactions with other drugs that may be taken that inhibit or induce CYP3A4 (Zytiga™ Full Prescribing Information, 2012, Janssen Biotech Inc., Section 7.2).

The development of soluble abiraterone derivatives would allow for IV dosing, which bypasses the liver, and can alleviate some of the aforementioned problems. PCT application WO 2015/200837 has disclosed water-soluble complexes of the abiraterone derivatives with serum albumin.

Accordingly, there is a clear and continuing need to create more soluble forms of abiraterone.

SUMMARY

An aspect of the current disclosure provides an abiraterone derivative, 2-(((3S,8R,9S,10R,13S,14S)-10,13-dimethyl-17-(pyridin-3-yl)-2,3,4,7,8,9,10,11,12,13,14,15-dodecahydro-1H-cyclopenta[a]phenanthren-3-yl)oxy)-2-oxoacetic acid (ABOA), which has the following chemical structure:

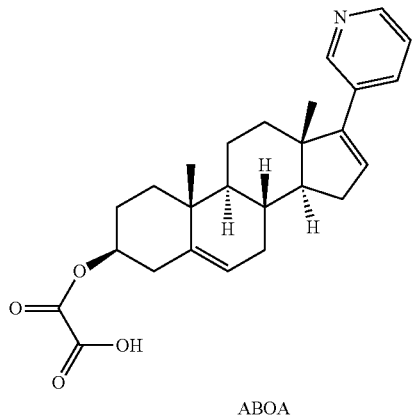

ABOA

Also, provided herein is a composition comprising a non-covalently bound complex comprising ABOA and human serum albumin, wherein the ABOA and the human serum albumin in the composition have a ratio by weight from about 1:1 to about 1:2000.

In some embodiments, the ABOA and the human serum albumin in the composition have a molar ratio from about 50:1 to about 1:10, from about 40:1 to about 1:9; from about 30:1 to about 1:8, from about 20:1 to about 1:7, from about 15:1 to about 1:6, from about 12:1 to about 1:5, from about 10:1 to about 1:4, from about 9:1 to about 1:3, from about 8:1 to about 1:2, from about 7:1 to about 1:2, from about 7:1 to about 1:1.5, or from about 6:1 to about 1:1.1. In some embodiments, the ABOA and the human serum albumin in the composition have a molar ratio of about 10:1, about 8:1, about 7:1, about 6:1, about 5.5:1, about 5:1, about 4.8:1, about 4.5:1, about 4.2:1, about 4:1, about 3.8:1, about 3.5:1, about 3:1, about 2.5:1, about 2:1, about 1.9:1, about 1.5:1, about 1.3:1, about 1:1, about 1:1.1, about 1:1.5, about 1:2, about 1:5, or about 1:10.

In some embodiments, the ABOA and the human serum albumin in the composition have a ratio by weight from about 1:5 to about 1:1000, from about 1:10 to about 1:800, from about 1:20 to about 1:600, from about 1:30 to about 1:500, from about 1:30 to about 1:400, from about 1:30 to about 1:300, from about 1:30 to about 1:250, from about 1:30 to about 1:200, from about 1:30 to about 1:150, 1:30 to about 1:140, from about 1:30 to about 1:130, from about 1:30 to about 1:120, from about 1:30 to about 1:110, 1:30 to about 1:100, 1:30 to about 1:90, from about 1:30 to about 1:80, from about 1:30 to about 1:70, from about 1:30 to about 1:60, from about 1:35 to about 1:500, from about 1:35 to about 1:400, from about 1:35 to about 1:300, from about 1:35 to about 1:250, from about 1:35 to about 1:200, from about 1:35 to about 1:150, 1:35 to about 1:140, from about 1:35 to about 1:130, from about 1:35 to about 1:120, from about 1:35 to about 1:110, 1:35 to about 1:100, 1:35 to about 1:90, from about 1:35 to about 1:80, from about 1:35 to about 1:70, from about 1:35 to about 1:60, from about 1:40 to about 1:500, from about 1:40 to about 1:400, from about 1:40 to about 1:300, from about 1:40 to about 1:250, from about 1:40 to about 1:200, from about 1:40 to about 1:150, 1:40 to about 1:140, from about 1:40 to about 1:130, from about 1:40 to about 1:120, from about 1:40 to about 1:110, 1:40 to about 1:100, 1:40 to about 1:90, from about 1:40 to about 1:80, from about 1:40 to about 1:70, or from about 1:40 to about 1:60. In some embodiments, the ABOA and the human serum albumin have a ratio by weight of about 1:20, about 1:30, about 1:35, about 1:40, about 1:45, about 1:50, about 1:55, about 1:60, about 1:65, about 1:70, about 1:75, about 1:80, about 1:90, about 1:100, about 1:110, about 1:120, about 1:130, or about 1:140, about 1:150, about 1:160, about 1:170, about 1:180, about 1:190, about 1:200, about 1:210, about 1:220, about 1:230, about 1:240, about 1:250, or about 1:275, about 1:300, about 1:350, about 1:400, about 1:450, or about 1:500.

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free.

Also, provided herein is a composition comprising ABOA and human serum albumin, wherein the ABOA and the human serum albumin in the composition have a ratio by weight from about 1:1 to about 1:2000.

In some embodiments, the ABOA and the human serum albumin in the composition have a ratio by weight from about 1:5 to about 1:1000, from about 1:10 to about 1:800, from about 1:20 to about 1:600, from about 1:30 to about 1:500, from about 1:30 to about 1:400, from about 1:30 to about 1:300, from about 1:30 to about 1:250, from about 1:30 to about 1:200, from about 1:30 to about 1:150, 1:30 to about 1:140, from about 1:30 to about 1:130, from about 1:30 to about 1:120, from about 1:30 to about 1:110, 1:30 to about 1:100, 1:30 to about 1:90, from about 1:30 to about 1:80, from about 1:30 to about 1:70, from about 1:30 to about 1:60, from about 1:35 to about 1:500, from about 1:35 to about 1:400, from about 1:35 to about 1:300, from about 1:35 to about 1:250, from about 1:35 to about 1:200, from about 1:35 to about 1:150, 1:35 to about 1:140, from about 1:35 to about 1:130, from about 1:35 to about 1:120, from about 1:35 to about 1:110, 1:35 to about 1:100, 1:35 to about 1:90, from about 1:35 to about 1:80, from about 1:35 to about 1:70, from about 1:35 to about 1:60, from about 1:40 to about 1:500, from about 1:40 to about 1:400, from about 1:40 to about 1:300, from about 1:40 to about 1:250, from about 1:40 to about 1:200, from about 1:40 to about 1:150, 1:40 to about 1:140, from about 1:40 to about 1:130, from about 1:40 to about 1:120, from about 1:40 to about 1:110, 1:40 to about 1:100, 1:40 to about 1:90, from about 1:40 to about 1:80, from about 1:40 to about 1:70, or from about 1:40 to about 1:60. In some embodiments, the ABOA and the human serum albumin have a ratio by weight of about 1:20, about 1:30, about 1:35, about 1:40, about 1:45, about 1:50, about 1:55, about 1:60, about 1:65, about 1:70, about 1:75, about 1:80, about 1:90, about 1:100, about 1:110, about 1:120, about 1:130, or about 1:140, about 1:150, about 1:160, about 1:170, about 1:180, about 1:190, about 1:200, about 1:210, about 1:220, about 1:230, about 1:240, about 1:250, or about 1:275, about 1:300, about 1:350, about 1:400, about 1:450, or about 1:500.

In some embodiments, the ABOA and the human serum albumin in the composition have a molar ratio from about 50:1 to about 1:10, from about 40:1 to about 1:9; from about 30:1 to about 1:8, from about 20:1 to about 1:7, from about 15:1 to about 1:6, from about 12:1 to about 1:5, from about 10:1 to about 1:4, from about 9:1 to about 1:3, from about 8:1 to about 1:2, from about 7:1 to about 1:2, from about 7:1 to about 1:1.5, or from about 6:1 to about 1:1.1. In some embodiments, the ABOA and the human serum albumin in the composition have a molar ratio of about 10:1, about 8:1, about 7:1, about 6:1, about 5.5:1, about 5:1, about 4.8:1, about 4.5:1, about 4.2:1, about 4:1, about 3.8:1, about 3.5:1, about 3:1, about 2.5:1, about 2:1, about 1.9:1, about 1.5:1, about 1.3:1, about 1:1, about 1:1.1, about 1:1.5, about 1:2, about 1:5, or about 1:10.

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free.

In some embodiments, the composition is a clear aqueous solution when the composition is dissolved in an aqueous solution. In some embodiments, the aqueous solution is substantially free of solvent other than water. In some embodiments, the aqueous solution is free of solvent other than water.

In some embodiments, the composition is a clear aqueous solution for at least about 1 hour, 2 hours, 3 hours, 4 hours, 5 hours, 6 hours, 8 hours, or 24 hours, when the composition is dissolved in an aqueous solution.

In some embodiments, the composition is a solid formulation. For example, the solid formulation can be produced in a uniform manner by lyophilization. A skilled artisan would recognize other methods, such as rotary evaporation, that can also produce solid formulations.

In some embodiments, the composition is an aqueous formulation. In some embodiments, the aqueous formulation is substantially free of solvent other than water. In some embodiments, the aqueous formulation is free of solvent other than water.

In some embodiments, the aqueous formulation is a clear aqueous solution. For example, the formulation can be a clear and stable aqueous solution reconstituted from a sterile lyophilized powder. In some embodiments, the aqueous formulation is a clear aqueous solution, wherein the aqueous formulation is substantially free of solvent other than water. In some embodiments, the aqueous formulation is a clear aqueous solution, wherein the aqueous formulation is free of solvent other than water. In some embodiments, the aqueous formulation is a clear aqueous solution for at least 1 hour, 2 hours, 3 hours, 4 hours, 5 hours, 6 hours, 8 hours, or 24 hours. In some embodiments, the solution remains clear for at least about 2 hours, 4 hours, 6 hours, 8 hours, 10 hours, 12 hours, 20 hours, 24 hours, 2 days, 3 days, 4 days, 5 days, 6 days or a week.

Also, provided herein is a pharmaceutical composition comprising the composition comprising the ABOA and the human serum albumin as described herein, and a pharmaceutically acceptable carrier.

In some embodiments, the pharmaceutical composition is free of a surfactant, such as CREMOPHOR® surfactants and Polysorbate 80. In some embodiments, the pharmaceutical composition is substantially free of a surfactant, such as CREMOPHOR® surfactants and Polysorbate 80. In some embodiments, the pharmaceutical composition can be substantially free of a surfactant selected from the group consisting of CREMOPHOR® surfactants and Polysorbate 80.

Also, provided herein is a method of treating a cancer, the method comprising the step of administering to a subject in need thereof of a therapeutically effective amount of a pharmaceutical composition comprising the composition comprising the ABOA and the human serum albumin as described herein, and a pharmaceutically acceptable carrier.

In some embodiments, the cancer is a prostate cancer. In some embodiments, the cancer is a metastatic castration-resistant prostate cancer.

Also, provided herein is a liquid pharmaceutical composition comprising the composition comprising the ABOA and the human serum albumin as described herein, and a pharmaceutically acceptable carrier.

In some embodiments, the liquid pharmaceutical composition is a reconstituted solution, reconstituted from the solid composition comprising the ABOA and the human serum albumin as described herein.

In some embodiments, the liquid pharmaceutical composition is an injectable pharmaceutical formulation.

Also, provided herein is a composition consisting essentially of ABOA and human serum albumin, wherein the ABOA and the human serum albumin in the composition have a ratio by weight from about 1:1 to about 1:2000.

In some embodiments, the ABOA and the human serum albumin in the composition have a ratio by weight from about 1:5 to about 1:1000, from about 1:10 to about 1:800, from about 1:20 to about 1:600, from about 1:30 to about 1:500, from about 1:30 to about 1:400, from about 1:30 to about 1:300, from about 1:30 to about 1:250, from about 1:30 to about 1:200, from about 1:30 to about 1:150, 1:30 to about 1:140, from about 1:30 to about 1:130, from about 1:30 to about 1:120, from about 1:30 to about 1:110, 1:30 to about 1:100, 1:30 to about 1:90, from about 1:30 to about 1:80, from about 1:30 to about 1:70, from about 1:30 to about 1:60, from about 1:35 to about 1:500, from about 1:35 to about 1:400, from about 1:35 to about 1:300, from about 1:35 to about 1:250, from about 1:35 to about 1:200, from about 1:35 to about 1:150, 1:35 to about 1:140, from about 1:35 to about 1:130, from about 1:35 to about 1:120, from about 1:35 to about 1:110, 1:35 to about 1:100, 1:35 to about 1:90, from about 1:35 to about 1:80, from about 1:35 to about 1:70, from about 1:35 to about 1:60, from about 1:40 to about 1:500, from about 1:40 to about 1:400, from about 1:40 to about 1:300, from about 1:40 to about 1:250, from about 1:40 to about 1:200, from about 1:40 to about 1:150, 1:40 to about 1:140, from about 1:40 to about 1:130, from about 1:40 to about 1:120, from about 1:40 to about 1:110, 1:40 to about 1:100, 1:40 to about 1:90, from about 1:40 to about 1:80, from about 1:40 to about 1:70, or from about 1:40 to about 1:60. In some embodiments, the ABOA and the human serum albumin have a ratio by weight of about 1:20, about 1:30, about 1:35, about 1:40, about 1:45, about 1:50, about 1:55, about 1:60, about 1:65, about 1:70, about 1:75, about 1:80, about 1:90, about 1:100, about 1:110, about 1:120, about 1:130, or about 1:140, about 1:150, about 1:160, about 1:170, about 1:180, about 1:190, about 1:200, about 1:210, about 1:220, about 1:230, about 1:240, about 1:250, or about 1:275, about 1:300, about 1:350, about 1:400, about 1:450, or about 1:500.

DETAILED DESCRIPTION

Abiraterone acetate oxoacetic acid (ABOA), pharmaceutically acceptable salts, compositions and methods of making thereof.

An aspect of the current disclosure provides an abiraterone derivative, 2-(((3S,8R,9S,10R,13S,14S)-10,13-dimethyl-17-(pyridin-3-yl)-2,3,4,7,8,9,10,11,12,13,14,15-dodecahydro-1H-cyclopenta[a]phenanthren-3-yl)oxy)-2-oxoacetic acid (ABOA), which has the following chemical structure:

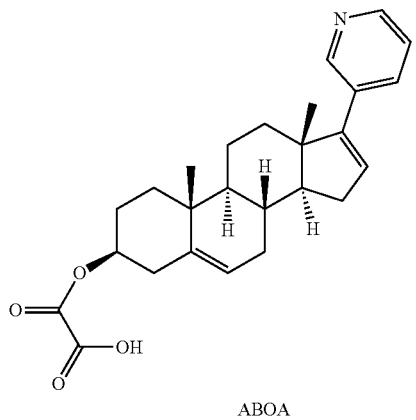

ABOA

ABOA is a white to off-white solid and is practically insoluble in water.

In some embodiments, the ABOA is a pharmaceutically acceptable salt of ABOA. In some embodiments, the ABOA is a hydrochloride salt of ABOA.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively. In some embodiments, pharmaceutically acceptable salts may be preferred over the respective free base or free acid because such salts impart greater stability or solubility to the molecule thereby facilitating formulation into a dosage form. Basic compounds are generally capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), napthalene-2-sulfonate, ethanedisulfonate, hydrogen bisulfide, bitartrate, gluconate, glucuronate, para-bromophenylsulfonate, carbonate, pyrosulfate, sulfite, bisulfate, monohydrogen phosphate, dihydrogen phosphate, metaphosphate, pyrophosphate, chloride, bromide, iodide, decanoate, caprylate, caprate, propiolate, suberate, sebacate, butyne-1,4-dioate, hexyne-1,6-dioate, terephthalate, sulfonate, xylenesulfonate, phenylpropionate, phenylbutyrate, β-hydroxybutyrate, glycolate, propanesulfonate, naphthalene-1-sulfonate, naphthalene-2-sulfonate and 2,5-dihydroxybenzoate. Suitable bases include pharmaceutically acceptable inorganic bases and pharmaceutically acceptable organic bases. Representative pharmaceutically acceptable base addition salts include hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—(C1-C6)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, ABOA is crystalline. In some embodiments, ABOA is in amorphous.

ABOA is a prodrug of abiraterone. After administration to patients, ABOA can be cleaved by in vivo enzymes to produce the pharmaceutically active substance abiraterone, similar to abiraterone acetate.

ABOA can be synthesized from abiraterone. In some embodiments, ABOA is synthesized from abiraterone. In some embodiments, ABOA is synthesized from abiraterone and oxalyl monohalides. In some embodiments, ABOA is synthesized from abiraterone and activated esters of oxalic acid.

A non-limiting example of synthesis of ABOA is shown in the scheme 1. In some embodiments, ABOA is prepared from abiraterone and oxalyl chloride.

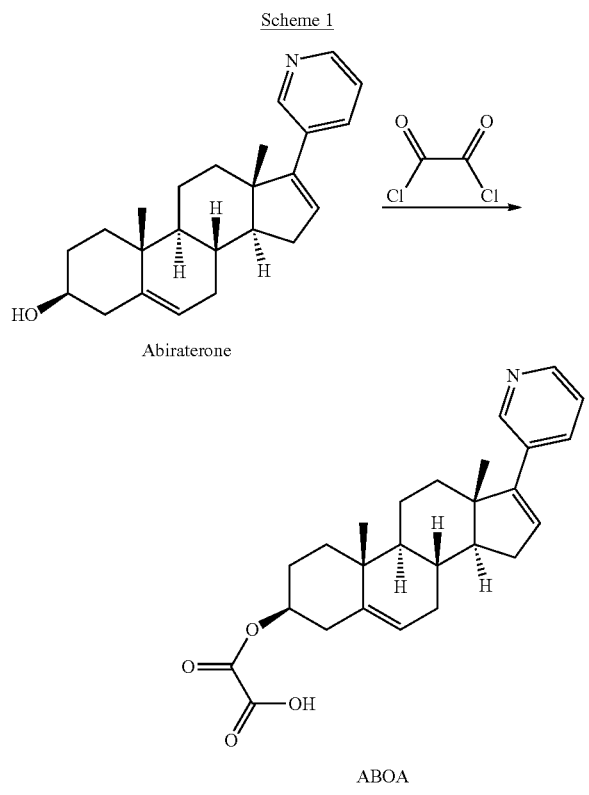

Scheme 1

Syntheses of abiraterone and related compounds have been reported by others. For example, U.S. Pat. Nos. 8,338,588; 8,076,474; and 5,604,213 describe methods for the synthesis of abiraterone and are hereby incorporated by reference in its entirety.

Also, provided herein is a pharmaceutical composition comprising ABOA, or a pharmaceutically acceptable salt thereof as described herein, and a pharmaceutically acceptable carrier. The pharmaceutical composition comprising the ABOA can be administered to an individual, such as human, via various routes, such as parenterally, including intravenous (e.g., as an infusion), intra-arterial, intraperitoneal, intrapulmonary, oral, inhalation, intravesicular, intramuscular, intra-tracheal, subcutaneous, intraocular, intrathecal, or transdermal route. In making the compositions comprising ABOA, the active ingredient is typically mixed with a pharmaceutically acceptable carrier (e.g., an excipient), diluted by a pharmaceutically acceptable carrier or enclosed within such a pharmaceutically acceptable carrier in the form of, for example, a capsule, sachet, paper, or other container. When the pharmaceutically acceptable carrier serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of ABOA, soft and hard gelatin capsules, suppositories, sterile injectable solutions, and sterile packaged powders. In preparing a formulation, the ABOA can be milled to provide the appropriate particle size prior to combining with the other ingredients. For example, ABOA can be milled to a particle size of less than 200 mesh. Some examples of suitable pharmaceutically acceptable carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The pharmaceutical compositions comprising ABOA can be formulated so as to provide quick, sustained or delayed release of the active ingredient after administration to the patient by employing procedures known in the art. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the pharmaceutical composition comprising ABOA (e.g., in a unit dosage form) may contain from about 5 to about 5000 mg of ABOA. In some embodiments, the effective amount of ABOA is from about 10 mg to about 500 mg, from about 20 mg to about 400 mg, from about 30 mg to about 350 mg, from about 40 mg to about 300 mg, from about 50 mg to about 250 mg, from about 50 mg to about 4000 mg, from about 100 mg to about 3000 mg, from about 150 mg to about 2000 mg, from about 200 mg to about 1500 mg, or from about 250 mg to about 1000 mg. In some embodiments, the effective amount of ABOA is about 50 mg, about 100 mg, about 150 mg, about 200 mg, about 250 mg, about 300 mg, about 350 mg, about 400 mg, about 450 mg, about 500 mg, about 750 mg, about 1000 mg, about 1250 mg, about 1500 mg, or about 2000 mg.

When the pharmaceutical composition comprising the ABOA is administered to the subject by an injection or an infusion, the term "pharmaceutically acceptable carrier" refers to any solution used to solubilize and deliver an agent to a subject. A desirable pharmaceutically acceptable carrier is saline. The pharmaceutically acceptable carrier may be 5% dextrose aqueous solution or a pharmaceutically acceptable or phisiological buffer. Other pharmaceutically acceptable carriers and their formulations are known to one skilled in the art and described, for example, in Remington's Pharmaceutical Sciences. (20$^{th}$ edition), ed. A. Gennaro, 2003, Lippincon Williams & Wilkins.

Pharmaceutically acceptable carriers that may be used in the pharmaceutical compositions of the present application include, but are not limited to, ion exchangers, alumina, aluminum stearate, lecithin, serum proteins (other than HSA), buffer substances such as phosphates, glycine, sorbic acid, potassium sorbate, salts or electrolytes, such as protamine sulfate, disodium hydrogen phosphate, potassium hydrogen phosphate, sodium chloride, zinc salts, colloidal silica, magnesium tri silicate, and cellulose-based substances.

Complexes comprising ABOA and human serum albumin and compositions thereof.

Also, provided herein is a composition comprising a non-covalently bound complex comprising ABOA and human serum albumin, wherein the ABOA and the human serum albumin in the composition have a ratio by weight from about 1:1 to about 1:2000.

In some embodiments, the ABOA and the human serum albumin in the composition have a ratio by weight from about 1:5 to about 1:1000, from about 1:10 to about 1:800, from about 1:20 to about 1:600, from about 1:30 to about 1:500, from about 1:30 to about 1:400, from about 1:30 to about 1:300, from about 1:30 to about 1:250, from about 1:30 to about 1:200, from about 1:30 to about 1:150, from about 1:30 to about 1:140, from about 1:30 to about 1:130, from about 1:30 to about 1:120, from about 1:30 to about 1:110, from about 1:30 to about 1:100, from about 1:30 to about 1:90, from about 1:30 to about 1:80, from about 1:30 to about 1:70, from about 1:30 to about 1:60, from about 1:35 to about 1:500, from about 1:35 to about 1:400, from about 1:35 to about 1:300, from about 1:35 to about 1:250, from about 1:35 to about 1:200, from about 1:35 to about 1:150, 1:35 to about 1:140, from about 1:35 to about 1:130, from about 1:35 to about 1:120, from about 1:35 to about 1:110, from about 1:35 to about 1:100, from about 1:35 to about 1:90, from about 1:35 to about 1:80, from about 1:35 to about 1:70, from about 1:35 to about 1:60, from about 1:40 to about 1:500, from about 1:40 to about 1:400, from about 1:40 to about 1:300, from about 1:40 to about 1:250, from about 1:40 to about 1:200, from about 1:40 to about 1:150, from about 1:40 to about 1:140, from about 1:40 to about 1:130, from about 1:40 to about 1:120, from about 1:40 to about 1:110, from about 1:40 to about 1:100, from about 1:40 to about 1:90, from about 1:40 to about 1:80, from about 1:40 to about 1:70, or from about 1:40 to about 1:60. In some embodiments, the ABOA and the human serum albumin have a ratio by weight of about 1:20, about 1:30, about 1:35, about 1:40, about 1:45, about 1:50, about 1:55, about 1:60, about 1:65, about 1:70, about 1:75, about 1:80, about 1:90, about 1:100, about 1:110, about 1:120, about 1:130, or about 1:140, about 1:150, about 1:160, about 1:170, about 1:180, about 1:190, about 1:200, about 1:210, about 1:220, about 1:230, about 1:240, about 1:250, or about 1:275, about 1:300, about 1:350, about 1:400, about 1:450, or about 1:500.

In some embodiments, the ABOA and the human serum albumin in the composition have a molar ratio from about 50:1 to about 1:10, from about 1:40:1 to about 1:9; from about 30:1 to about 1:8, from about 20:1 to about 1:7, from about 15:1 to about 1:6, from about 12:1 to about 1:5, from about 10:1 to about 1:4, from about 9:1 to about 1:3, from about 8:1 to about 1:2, from about 7:1 to about 1:2, from about 7:1 to about 1:1.5, or from about 6:1 to about 1:1.1. In some embodiments, the ABOA and the human serum albumin in the composition have a molar ratio of about 10:1, about 8:1, about 7:1, about 6:1, about 5.5:1, about 5:1, about 4.8:1, about 4.5:1, about 4.2:1, about 4:1, about 3.8:1, about 3.5:1, about 3:1, about 2.5:1, about 2:1, about 1.9:1, about 1.5:1, about 1.3:1, about 1:1, about 1:1.1, about 1:1.5, about 1:2, about 1:5, or about 1:10.

In some embodiments, the non-covalent interaction between ABOA and human serum albumin in the complex comprises hydrogen bonding. In some embodiments, the non-covalent interaction between ABOA and human serum albumin in the complex comprises electrostatic interaction. In some embodiments, the non-covalent interaction between ABOA and human serum albumin in the complex comprises hydrophobic interaction. In some embodiments, the non-covalent interaction between ABOA and human serum albumin in the complex comprises Van der Waals forces. In some embodiments, the non-covalent interaction between ABOA and human serum albumin in the complex comprises hydrogen bonding, electrostatic interaction, hydrophobic interactions and Van der Waals forces.

In some embodiments, the non-covalent interaction between ABOA and human serum albumin in the composition comprises hydrogen bonding. In some embodiments, the non-covalent interaction between ABOA and human serum albumin in the composition comprises electrostatic interaction. In some embodiments, the non-covalent interaction between ABOA and human serum albumin in the composition comprises hydrophobic interaction. In some embodiments, the non-covalent interaction between ABOA and human serum albumin in the composition comprises Van der Waals forces. In some embodiments, the non-covalent interaction between ABOA and human serum albumin in the composition comprises hydrogen bonding, electrostatic interaction, hydrophobic interactions and Van der Waals forces.

As used herein, the term "human serum albumin" refers to native and recombinant human serum albumin. Native human serum albumin and other plasma proteins can be precipitated from human plasma by varying the pH and adding ethanol, in what is known as the Cohn fractionation process (Cohn E J et al., *J. Am. Chem. Soc.* 1946; 68:459-475). By controlling the pH and ethanol content, semi-purified fractions of plasma proteins can be produced. One of the last proteins to precipitate in the Cohn process is native human serum albumin. After precipitation, a wet paste of crude native human serum albumin is obtained. Subsequent bioprocessing steps (purification, filtration, pasteurization, etc.) can be used to produce a purified, stabilized form of native human serum albumin for commercial use (Lin J J et al., *Pharmaceutical Research* 2000; 17:391-6). Recombinant human serum albumin is a highly purified animal-, virus-, and prion-free product as alternative to native human serum albumin, to which it is structurally equivalent (Bosse D et al., *J Clin. Pharmacol.* 2005; 45:57-67). Recombinant human serum albumin has been produced by various hosts, both prokaryotic and eukaryotic (Chen Z et al., *Biochimica et Biophysica Acta* 2013; 1830:5515-5525). A fatty acid free human serum albumin can be prepared by treatment of human serum albumin with charcoal at low pH. Likewise, treatment of human serum albumin with charcoal at low pH can be used to remove fatty acids from human serum albumin (Chen R F, *J Biol. Chem.* 1967; 242:173-181).

Human serum albumin (HSA) is a highly soluble globular protein of Mr 65K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Intravenous use of HSA solution has been indicated for the prevention and treatment of hypovolumic shock (see, e.g., Tullis, *JAMA,* 237, 355-360, 460-463, (1977) and Houser et al., *Surgery, Gynecology and Obstetrics,* 150, 811-816 (1980)) and in conjunction with exchange transfusion in the treatment of neonatal hyperbilirubinemia (see, e.g., Finlayson, *Seminars in Thrombosis and Hemostasis,* 6, 85-120, (1980)).

Human serum albumin (HSA) has multiple hydrophobic binding sites (a total of seven for medium and long-chain fatty acids, an endogenous ligand of HSA) and binds a diverse set of drugs, especially neutral and negatively charged hydrophobic compounds (Goodman et al., *The Pharmacological Basis of Therapeutics,* 9th ed, *McGraw-Hill* New York (1996)). Two high affinity binding sites have been proposed in subdomains IIA and IIIA of HSA, which are highly elongated hydrophobic pockets with charged lysine and arginine residues near the surface which function as attachment points for polar ligand features (see, e.g., Fehske et al., *Biochem. Pharmcol.,* 30, 687-92 (1981), Vorum, *Dan. Med. Bull.,* 46, 379-99 (1999), Kragh-Hansen, *Dan. Med Bull.,* 1441, 131-40 (1990), Curry et al., *Nat. Struct. Biol.,* 5, 827-35 (1998), Sugio et al., *Protein. Eng.,* 12, 439-46 (1999), He et al., *Nature,* 358, 209-15 (1992), and Carter et al., *Adv. Protein. Chem.,* 45, 153-203 (1994)).

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free. In some embodiments, the human serum albumin contains no more than two moles of fatty acids bound to one mole of human serum albumin. In some embodiments, the human serum albumin contains no more than one mole of fatty acids bound to one mole of human serum albumin. In some embodiments, human serum albumin contains no more than 0.5 moles of fatty acids bound to one mole of human serum albumin. In some embodiments, the human serum albumin contains no more than 0.1 moles of fatty acids bound to one mole of human serum albumin. In some embodiments, the human serum albumin contains no more than 0.05 moles of fatty acids bound to one mole of human serum albumin. In some embodiments, the human serum albumin contains no more than 0.01 moles of fatty acids bound to one mole of human serum albumin. In some embodiments, the human serum albumin contains no more than 0.001 moles of fatty acids bound to one mole of human serum albumin. In some embodiments, the human serum albumin contains no more than 0.0005 moles of fatty acids bound to one mole of human serum albumin. In some embodiments, the human serum albumin contains no more than 0.0001 moles of fatty acids bound to one mole of human serum albumin.

As used herein, the term "non-covalently bound complex" refers to a complex in which the bonds between the components of the complex are non-covalent bonds (e.g., weak bonds such as hydrogen bonds, electrostatic effects, π-effects, hydrophobic effects and Van der Waals forces). Further, human serum albumin (HSA) has multiple hydrophobic binding sites (a total of seven for medium and long-chain fatty acids, an endogenous ligand of HSA) and binds a diverse set of drugs, especially neutral and negatively charged hydrophobic compounds (Goodman et al., The Pharmacological Basis of Therapeutics, 9th ed, McGraw-Hill New York (1996)). Additionally, after the drug molecule binds to HSA, the drug molecule and HSA form a non-covalently bound drug and protein complex through the binding sites of HSA. This concept is commonly understood by one of ordinary skill in the art to which this disclosure belongs. One example of a non-covalently bound complex is a non-covalently bound complex of HSA and fatty acids, in which the fatty acids bind to HSA through HSA's multiple binding sites.

As used herein, the term "stable" refers to non-covalently bound complexes that do not readily disassociate and aggregate into their separate parts, e.g., do not readily dissociate and aggregate for a period of time of greater than 6 hours, 12 hours, 24 hours, or 3 days). For example, a solution including stable non-covalently bound complexes will often appear transparent whereas a solution including unstable non-covalently bound complexes will appear translucent or cloudy. Further, it will be appreciated by those of ordinary skill in the art, that after a period of time, stable non-covalently bound complexes can disassociate and aggregate into their separate parts. Thus, a solution including stable non-covalently bound complexes can become translucent or cloudy after a period of time (e.g., 6 hours, 12 hours, 24 hours, or 3 days).

As used herein, the term "essentially fatty acid free" refers to proteins (e.g. serum albumin) that contain less than about 0.02% fatty acid by weight. For example, human serum albumin that is essentially fatty acid free can contain less than 0.02% fatty acid by weight.

As used herein, the term "fatty acids" refers to non-esterified fatty acids (e.g. linoleic acid, α-linoleic acid, γ-linoleic acid).

In some embodiments, the composition is a clear aqueous solution when the composition is dissolved in an aqueous solution. In some embodiments, the aqueous solution is substantially free of solvent other than water. In some embodiments, the aqueous solution is free of solvent other than water.

In some embodiments, the composition is a clear aqueous solution when the composition is dissolved in water. In some embodiments, the composition is a clear aqueous solution when the composition is dissolved in 0.9% saline. In some embodiments, the composition is a clear aqueous solution when the composition is dissolved in 5% Dextrose solution.

As used herein, the term "aqueous solution" refers to a solution, wherein at least one solvent is water and the weight % of water in the mixture of solvents is at least 50%, at least 60%, at least 70% or at least 90%. In some embodiments, aqueous solution is a solution in which water is the only solvent. In some embodiments, aqueous solution is 0.9% saline. In some embodiments, aqueous solution is 5% Dextrose solution. In some embodiments, aqueous solution is a buffer (e.g., phosphate buffer or a carbonate buffer). In some embodiments, the buffer is physiological buffer or a pharmaceutically acceptable buffer. In some embodiments, the buffer is any one of buffers described, for example, in Y.-C.

Lee et al. International Journal of Pharmaceutics 253 (2003) 111-119, the disclosure of which is incorporated herein by reference in its entirety. In some embodiments, the buffer comprises maleic acid, tartaric acid, lactic acid, citric acid, acetic acid, sodium bicarbonate, sodium phosphate, or mixtures thereof. In some embodiments, the pH range of the buffer is from about 3 to about 9, from about 4 to about 8, from about 5 to about 7, from about 6.0 to about 6.5, from about 6 to about 7, from about 3 to about 5, from about 3 to about 7, from about 4 to about 6, or from about 5 to about 6. In some embodiments, the pH of the buffer is about 4, about 5, about 6, about 6.1, about 6.2, about 6.3, about 6.4, about 6.5, about 6.6, about 6.7, about 6.8, about 6.9, about 7.0, about 7.5, or about 8.

As used herein, the term "aqueous solvent" refer to a liquid comprising at least 50%, at least 60%, at least 70%, at least 90% or at least 95% water. In some embodiments, aqueous solvent is water, 0.9% saline or 5% dextrose.

In some embodiments, the composition forms a clear aqueous solution, when the composition is dissolved in an aqueous solution, wherein the clear aqueous solution has pH value from about 5 to about 8. In some embodiments, the composition forms a clear aqueous solution, when the composition is dissolved in an aqueous solution, wherein the clear aqueous solution has pH value from about 5.5 to about 7.8. In some embodiments, the composition forms a clear aqueous solution, when the composition is dissolved in an aqueous solution, wherein the clear aqueous solution has pH value from about 6 to about 7.5. In some embodiments, the composition forms a clear aqueous solution, when the composition is dissolved in an aqueous solution, wherein the clear aqueous solution has pH value from about 6.5 to about 7.5. In some embodiments, the composition forms a clear aqueous solution, when the composition is dissolved in an aqueous solution, wherein the clear aqueous solution has pH value from about 6 to about 6.5. In some embodiments, the composition forms a clear aqueous solution, when the composition is dissolved in an aqueous solution, wherein the clear aqueous solution has pH value from about 6.5 to about 7. In some embodiments, the composition forms a clear aqueous solution, when the composition is dissolved in an aqueous solution, wherein the clear aqueous solution has pH value from about 7 to about 7.5. In some embodiments, the composition forms a clear aqueous solution, when the composition is dissolved in an aqueous solution, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous solution is substantially free of solvent other than water. In some embodiments, the aqueous solution is free of solvent other than water.

In some embodiments, the composition forms a clear aqueous solution, when the composition is dissolved in water, wherein the clear aqueous solution has pH value from about 5 to about 8. In some embodiments, the composition forms a clear aqueous solution, when the composition is dissolved in water, wherein the clear aqueous solution has pH value from about 5.5 to about 7.8. In some embodiments, the composition forms a clear aqueous solution, when the composition is dissolved in water, wherein the clear aqueous solution has pH value from about 6 to about 7.5. In some embodiments, the composition forms a clear aqueous solution, when the composition is dissolved in water, wherein the clear aqueous solution has pH value from about 6.5 to about 7.5. In some embodiments, the composition forms a clear aqueous solution, when the composition is dissolved in water, wherein the clear aqueous solution has pH value from about 6 to about 6.5. In some embodiments, the composition forms a clear aqueous solution, when the composition is dissolved in water, wherein the clear aqueous solution has pH value from about 6.5 to about 7. In some embodiments, the composition forms a clear aqueous solution, when the composition is dissolved in water, wherein the clear aqueous solution has pH value from about 7 to about 7.5. In some embodiments, the composition forms a clear aqueous solution, when the composition is dissolved in water, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

In some embodiments, the composition forms a clear aqueous solution, when the composition is dissolved in 0.9% saline, wherein the clear aqueous solution has pH value from about 5 to about 8. In some embodiments, the composition forms a clear aqueous solution, when the composition is dissolved in 0.9% saline, wherein the clear aqueous solution has pH value from about 5.5 to about 7.8. In some embodiments, the composition forms a clear aqueous solution, when the composition is dissolved in 0.9% saline, wherein the clear aqueous solution has pH value from about 6 to about 7.5. In some embodiments, the composition forms a clear aqueous solution, when the composition is dissolved in 0.9% saline, wherein the clear aqueous solution has pH value from about 6.5 to about 7.5. In some embodiments, the composition forms a clear aqueous solution, when the composition is dissolved in 0.9% saline, wherein the clear aqueous solution has pH value from about 6 to about 6.5. In some embodiments, the composition forms a clear aqueous solution, when the composition is dissolved in 0.9% saline, wherein the clear aqueous solution has pH value from about 6.5 to about 7. In some embodiments, the composition forms a clear aqueous solution, when the composition is dissolved in 0.9% saline, wherein the clear aqueous solution has pH value from about 7 to about 7.5. In some embodiments, the composition forms a clear aqueous solution, when the composition is dissolved in 0.9% saline, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

In some embodiments, the composition forms a clear aqueous solution, when the composition is dissolved in 5% Dextrose solution, wherein the clear aqueous solution has pH value from about 5 to about 8. In some embodiments, the composition forms a clear aqueous solution, when the composition is dissolved in 5% Dextrose solution, wherein the clear aqueous solution has pH value from about 5.5 to about 7.8. In some embodiments, the composition forms a clear aqueous solution, when the composition is dissolved in 5% Dextrose solution, wherein the clear aqueous solution has pH value from about 6 to about 7.5. In some embodiments, the composition forms a clear aqueous solution, when the composition is dissolved in 5% Dextrose solution, wherein the clear aqueous solution has pH value from about 6.5 to about 7.5. In some embodiments, the composition forms a clear aqueous solution, when the composition is dissolved in 5% Dextrose solution, wherein the clear aqueous solution has pH value from about 6 to about 6.5. In some embodiments, the composition forms a clear aqueous solution, when the composition is dissolved in 5% Dextrose solution, wherein the clear aqueous solution has pH value from about 6.5 to about 7. In some embodiments, the composition forms a clear aqueous solution, when the composition is dissolved in 5% Dextrose solution, wherein the clear aqueous solution has pH value from about 7 to about 7.5. In some embodiments, the composition forms a clear aqueous solution, when the composition is dissolved in 5% Dextrose solution, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

In some embodiments, the term "clear aqueous solution" refers to an aqueous solution comprising ABOA and HSA, which is transparent upon visual observation and essentially free of visible particles or precipitation of undissolved ABOA. In some embodiments, "essentially free of visible particles or precipitation of undissolved ABOA" can be assessed as follows: after a clear aqueous solution is filtered with a 0.22 micron filter, the amount of ABOA in the filtered aqueous solution is at least 95% of the total amount of ABOA in the aqueous solution before filtration. The total amount of ABOA in the aqueous solution before filtration includes the particles or precipitation of undissolved ABOA in the aqueous solution or with the aqueous solution. The amount of the ABOA in an aqueous solution can be measured by the methods using HPLC. The methods of measuring the amount of the ABOA in an aqueous solution are illustrated in the experimental examples described herein. The methods are commonly understood by one of ordinary skill in the art to which this disclosure belongs.

When visually observed, for example, the term "clear aqueous solution" excludes a milky aqueous solution. Further, the term "clear aqueous solution" excludes a cloudy or hazy aqueous solution.

In some embodiments, when the composition comprising a non-covalently bound complex comprising ABOA and human serum albumin as described herein (e.g., sterile solid powder) is dissolved in an aqueous solvent (e.g., water, 0.9% saline or 5% dextrose), the resultant aqueous solution, when filtered using a 0.22 micron filter, comprises 100% at the time of preparation, at least 98.7% after 1 hour, at least 98.7% after 2 hours, at least 98.2% after 3 hours, at least 98.2% after 4 hours, at least 98.2% after 5 hours, or at least 98.2% after 6 hours of the amount of ABOA used to prepare the composition.

In some embodiments, when the composition comprising a non-covalently bound complex comprising ABOA and human serum albumin as described herein (e.g., sterile solid powder) is dissolved in an aqueous solvent (e.g., water, 0.9% saline or 5% dextrose), the resultant aqueous solution, when filtered using a 0.22 micron filter, comprises 99% at the time of preparation, at least 99% after 1 hour, at least 99% after 2 hours, at least 99% after 3 hours, at least 99% after 4 hours, at least 99% after 5 hours, or at least 99% after 6 hours of the amount of ABOA used to prepare the composition.

In some embodiments, when the composition comprising a non-covalently bound complex comprising ABOA and human serum albumin as described herein (e.g., sterile solid powder) is dissolved in an aqueous solvent (e.g., water, 0.9% saline or 5% dextrose), the resultant aqueous solution, when filtered using a 0.22 micron filter, comprises 98% at the time of preparation, at least 98% after 1 hour, at least 98% after 2 hours, at least 98% after 3 hours, at least 98% after 4 hours, at least 98% after 5 hours, at least 98% after 6 hours, or at least 98% after 24 hours of the amount of ABOA used to prepare the composition.

In some embodiments, when the composition comprising a non-covalently bound complex comprising ABOA and human serum albumin as described herein (e.g., sterile solid powder) is dissolved in an aqueous solvent (e.g., water, 0.9% saline or 5% dextrose), the resultant aqueous solution, when filtered using a 0.22 micron filter, comprises 97% at the time of preparation, at least 97% after 1 hour, at least 97% after 2 hours, at least 97% after 3 hours, at least 97% after 4 hours, at least 97% after 5 hours, at least 97% after 6 hours, or at least 97% after 24 hours of the amount of ABOA used to prepare the composition.

In some embodiments, when the composition comprising a non-covalently bound complex comprising ABOA and human serum albumin as described herein (e.g., sterile solid powder) is dissolved in an aqueous solvent (e.g., water, 0.9% saline or 5% dextrose), the resultant aqueous solution, when filtered using a 0.22 micron filter, comprises 96% at the time of preparation, at least 96% after 1 hour, at least 96% after 2 hours, at least 96% after 3 hours, at least 96% after 4 hours, at least 96% after 5 hours, at least 96% after 6 hours, or at least 96% after 24 hours of the amount of ABOA used to prepare the composition.

In some embodiments, when the composition comprising a non-covalently bound complex comprising ABOA and human serum albumin as described herein (e.g., sterile solid powder) is dissolved in an aqueous solvent (e.g., water, 0.9% saline or 5% dextrose), the resultant aqueous solution, when filtered using a 0.22 micron filter, comprises 95% at the time of preparation, at least 95% after 1 hour, at least 95% after 2 hours, at least 95% after 3 hours, at least 95% after 4 hours, at least 95% after 5 hours, at least 95% after 6 hours, or at least 95% after 24 hours of the amount of ABOA used to prepare the composition.

In some embodiments, the composition is a clear aqueous solution for at least about 1 hour, 2 hours, 3 hours, 4 hours, 5 hours, 6 hours, 8 hours, or 24 hours, when the composition is dissolved in an aqueous solution. In some embodiments, the composition is a clear aqueous solution for at least about 1 hour, 2 hours, 3 hours, 4 hours, 5 hours, 6 hours, 8 hours, or 24 hours, when the composition is dissolved in water. In some embodiments, the composition is a clear aqueous solution for at least about 1 hour, 2 hours, 3 hours, 4 hours, 5 hours, 6 hours, 8 hours, or 24 hours, when the composition is dissolved in 0.9% saline. In some embodiments, the composition is a clear aqueous solution for at least about 1 hour, 2 hours, 3 hours, 4 hours, 5 hours, 6 hours, 8 hours, or 24 hours, when the composition is dissolved in 5% Dextrose solution.

In some embodiments, the amount of ABOA that is bound to the HSA (e.g., non-covalently) in the aqueous solution (e.g., clear aqueous solution) comprising the composition comprising ABOA and HSA (as described herein) is at least 40%, at least 50%, at least 60%, at least 70%, at least 80%, at least 90%, at least 95%, at least 99%, or about 100% of the total about of ABOA in the aqueous solution.

In some embodiments, the composition is a solid formulation. For example, the solid formulation can be produced in a uniform manner by lyophilization. A skilled artisan would recognize other methods, such as rotary evaporation, that can also produce solid formulations.

In some embodiments, the composition is an aqueous formulation. In some embodiments, the aqueous formulation is substantially free of solvent other than water. In some embodiments, the aqueous formulation is free of solvent other than water.

In some embodiments, the aqueous formulation is a clear aqueous solution. For example, the formulation can be a clear and stable aqueous solution reconstituted from a sterile lyophilized powder. In some embodiments, the aqueous formulation is a clear aqueous solution, wherein the aqueous formulation is substantially free of solvent other than water.

In some embodiments, the aqueous formulation is a clear aqueous solution, wherein the aqueous formulation is free of solvent other than water.

In some embodiments, the aqueous formulation is a clear aqueous solution reconstituted from the solid formulation (e.g. the sterile lyophilized powder) in water. In some embodiments, the aqueous formulation is a clear aqueous solution reconstituted from the solid formulation (e.g. the sterile lyophilized powder) in 0.9% saline. In some embodiments, the aqueous formulation is a clear aqueous solution reconstituted from the solid formulation (e.g. the sterile lyophilized powder) in 5% Dextrose solution.

In some embodiments, the aqueous formulation is a clear aqueous solution reconstituted from the solid formulation (e.g. the sterile lyophilized powder) in water, wherein the aqueous formulation has pH value from about 5 to about 8. In some embodiments, the aqueous formulation is a clear aqueous solution reconstituted from the solid formulation (e.g. the sterile lyophilized powder) in 0.9% saline, wherein the aqueous formulation has pH value from about 5 to about 8. In some embodiments, the aqueous formulation is a clear aqueous solution reconstituted from the solid formulation (e.g. the sterile lyophilized powder) in 5% Dextrose solution, wherein the aqueous formulation has pH value from about 5 to about 8.

In some embodiments, the aqueous formulation is a clear aqueous solution reconstituted from the solid formulation (e.g. the sterile lyophilized powder) in water, wherein the aqueous formulation has pH value from about 6 to about 7.5. In some embodiments, the aqueous formulation is a clear aqueous solution reconstituted from the solid formulation (e.g. the sterile lyophilized powder) in 0.9% saline, wherein the aqueous formulation has pH value from about 6 to about 7.5. In some embodiments, the aqueous formulation is a clear aqueous solution reconstituted from the solid formulation (e.g. the sterile lyophilized powder) in 5% Dextrose solution, wherein the aqueous formulation has pH value from about 6 to about 7.5.

In some embodiments, the aqueous formulation has pH value from about 5 to about 8. In some embodiments, the aqueous formulation has pH value from about 5.5 to about 7.8. In some embodiments, the aqueous formulation has pH value from about 6 to about 7.5. In some embodiments, the aqueous formulation has pH value from about 6.5 to about 7.5. In some embodiments, the aqueous formulation has pH value from about 6 to about 6.5. In some embodiments, the aqueous formulation has pH value from about 6.5 to about 7. In some embodiments, the aqueous formulation has pH value from about 7 to about 7.5. In some embodiments, the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous formulation is substantially free of solvent other than water. In some embodiments, the aqueous formulation is free of solvent other than water.

In some embodiments, the aqueous formulation is a clear aqueous solution, wherein the aqueous formulation has pH value from about 5 to about 8, and wherein the aqueous formulation is substantially free of solvent other than water. In some embodiments, the aqueous formulation is a clear aqueous solution, wherein the aqueous formulation has pH value from about 5 to about 8, and wherein the aqueous formulation is free of solvent other than water. In some embodiments, the aqueous formulation is a clear aqueous solution, wherein the aqueous formulation has pH value from about 5.5 to about 7.8, and wherein the aqueous formulation is substantially free of solvent other than water. In some embodiments, the aqueous formulation is a clear aqueous solution, wherein the aqueous formulation has pH value from about 5.5 to about 7.8, and wherein the aqueous formulation is free of solvent other than water. In some embodiments, the aqueous formulation is a clear aqueous solution, wherein the aqueous formulation has pH value from about 6 to about 7.5, and wherein the aqueous formulation is substantially free of solvent other than water. In some embodiments, the aqueous formulation is a clear aqueous solution, wherein the aqueous formulation has pH value from about 6 to about 7.5, and wherein the aqueous formulation is free of solvent other than water. In some embodiments, the aqueous formulation is a clear aqueous solution, wherein the aqueous formulation has pH value from about 6.5 to about 7.5, and wherein the aqueous formulation is substantially free of solvent other than water. In some embodiments, the aqueous formulation is a clear aqueous solution, wherein the aqueous formulation has pH value from about 6.5 to about 7.5, and wherein the aqueous formulation is free of solvent other than water. In some embodiments, the aqueous formulation is a clear aqueous solution, wherein the aqueous formulation has pH value from about 6 to about 6.5, and wherein the aqueous formulation is substantially free of solvent other than water. In some embodiments, the aqueous formulation is a clear aqueous solution, wherein the aqueous formulation has pH value from about 6 to about 6.5, and wherein the aqueous formulation is free of solvent other than water. In some embodiments, the aqueous formulation is a clear aqueous solution, wherein the aqueous formulation has pH value from about 6.5 to about 7, and wherein the aqueous formulation is substantially free of solvent other than water. In some embodiments, the aqueous formulation is a clear aqueous solution, wherein the aqueous formulation has pH value from about 6.5 to about 7, and wherein the aqueous formulation is free of solvent other than water. In some embodiments, the aqueous formulation is a clear aqueous solution, wherein the aqueous formulation has pH value from about 7 to about 7.5, and wherein the aqueous formulation is substantially free of solvent other than water. In some embodiments, the aqueous formulation is a clear aqueous solution, wherein the aqueous formulation has pH value from about 7 to about 7.5, and wherein the aqueous formulation is free of solvent other than water. In some embodiments, the aqueous formulation is a clear aqueous solution, wherein the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5, and wherein the aqueous formulation is substantially free of solvent other than water. In some embodiments, the aqueous formulation is a clear aqueous solution, wherein the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5, and wherein the aqueous formulation is free of solvent other than water.

In some embodiments, the aqueous formulation is a clear aqueous solution for at least 1 hour. In some embodiments, the aqueous formulation is a clear aqueous solution for at least 2 hours. In some embodiments, the aqueous formulation is a clear aqueous solution for at least 3 hours. In some embodiments, the aqueous formulation is a clear aqueous solution for at least 4 hours. In some embodiments, the aqueous formulation is a clear aqueous solution for at least 5 hours. In some embodiments, the aqueous formulation is a clear aqueous solution for at least 6 hours. In some embodiments, the aqueous formulation is a clear aqueous solution for at least 8 hours. In some embodiments, the aqueous formulation is a clear aqueous solution for at least 24 hours. In some embodiments, the solution remains clear for at least about 2 hours, 4 hours, 6 hours, 8 hours, 10 hours, 12 hours, 20 hours, 24 hours, 2 days, 3 days, 4 days, 5 days, 6 days or a week. In some embodiments, the aqueous formulation is substantially free of solvent other than water. In some embodiments, the aqueous formulation is free of solvent other than water.

In some embodiments, after the aqueous formulation (e.g. a clear aqueous solution) is filtered by a 0.22 micron filter, the amount of ABOA in the filtered aqueous solution is at least 96% of the total amount of ABOA in the aqueous solution before the filtration. In some embodiments, after the aqueous formulation (e.g. a clear aqueous solution) is filtered by a 0.22 micron filter, the amount of ABOA in the filtered aqueous solution is at least 97% of the total amount of ABOA in the aqueous solution before the filtration. In some embodiments, after the aqueous formulation (e.g. a clear aqueous solution) is filtered by a 0.22 micron filter, the amount of ABOA in the filtered aqueous solution is at least 98% of the total amount of ABOA in the aqueous solution before the filtration. In some embodiments, after the aqueous formulation (e.g. a clear aqueous solution) is filtered by a 0.22 micron filter, the amount of ABOA in the filtered aqueous solution is at least 99% of the total amount of ABOA in the aqueous solution before the filtration. In some embodiments, after the aqueous formulation (e.g. a clear aqueous solution) is filtered by a 0.22 micron filter, the amount of ABOA in the filtered aqueous solution is at least 99.5% of the total amount of ABOA in the aqueous solution before the filtration. In some aspects of these embodiments, the aqueous formulation is filtered by a 0.22-micron filter at a time period selected from 1 hour, 2 hours, 3, hours, 4 hours, 5 hours, 6 hours, 12 hours, 18 hours and 24 hours. In some embodiments, the aqueous formulation is free of solvent other than water. In some embodiments, the aqueous formulation is substantially free of solvent other than water.

In some embodiments, after the aqueous formulation (e.g. a clear aqueous solution) is filtered by a 0.22 micron filter, the amount of ABOA in the filtered aqueous solution is at least 95%, 96%, 97%, 98%, 99%, or 99.5% of the total amount of ABOA in the aqueous solution before filtration, wherein the clear aqueous solution has pH value from about 5 to about 8, and wherein the clear aqueous solution is substantially free of solvent other than water. In some embodiments, after the aqueous formulation (e.g. a clear aqueous solution) is filtered by a 0.22 micron filter, the amount of ABOA in the filtered aqueous solution is at least 95%, 96%, 97%, 98%, 99%, or 99.5% of the total amount of ABOA in the aqueous solution before filtration, wherein the clear aqueous solution has pH value from about 6 to about 7.5, and wherein the clear aqueous solution is substantially free of solvent other than water. In some embodiments, after the aqueous formulation (e.g. a clear aqueous solution) is filtered by a 0.22 micron filter, the amount of ABOA in the filtered aqueous solution is at least 95%, 96%, 97%, 98%, 99%, or 99.5% of the total amount of ABOA in the aqueous solution before filtration, wherein the clear aqueous solution has pH value from about 5 to about 8, and wherein the clear aqueous solution is free of solvent other than water. In some embodiments, after the aqueous formulation (e.g. a clear aqueous solution) is filtered by a 0.22 micron filter, the amount of ABOA in the filtered aqueous solution is at least 95%, 96%, 97%, 98%, 99%, or 99.5% of the total amount of ABOA in the aqueous solution before filtration, wherein the clear aqueous solution has pH value from about 6 to about 7.5, and wherein the clear aqueous solution is free of solvent other than water. In some aspects of these embodiments, the aqueous formulation is filtered by a 0.22-micron filter at a time period selected from 1 hour, 2 hours, 3, hours, 4 hours, 5 hours, 6 hours, 12 hours, 18 hours and 24 hours.

In some embodiments, after the aqueous formulation is filtered by a 0.22 micron filter, the amount of ABOA in the filtered aqueous solution is at least 80% of the total amount of ABOA in the aqueous solution before the filtration. In some embodiments, after the aqueous formulation is filtered by a 0.22 micron filter, the amount of ABOA in the filtered aqueous solution is at least 85% of the total amount of ABOA in the aqueous solution before the filtration. In some embodiments, after the aqueous formulation is filtered by a 0.22 micron filter, the amount of ABOA in the filtered aqueous solution is at least 90% of the total amount of ABOA in the aqueous solution before the filtration. In some aspects of these embodiments, the aqueous formulation is filtered by a 0.22-micron filter at a time period selected from 1 hour, 2 hours, 3, hours, 4 hours, 5 hours, 6 hours, 12 hours, 18 hours and 24 hours. In some embodiments, the aqueous formulation is free of solvent other than water. In some embodiments, the aqueous formulation is substantially free of solvent other than water.

Also, provided herein is a pharmaceutical composition comprising the composition comprising a non-covalently bound complex comprising ABOA and human serum albumin as described herein, and a pharmaceutically acceptable carrier.

In some embodiments, the pharmaceutical composition is free of a surfactant, such as CREMOPHOR® surfactants and Polysorbate 80. In some embodiments, the pharmaceutical composition is substantially free of a surfactant, such as CREMOPHOR® surfactants and Polysorbate 80. In some embodiments, the pharmaceutical composition can be substantially free of a surfactant selected from the group consisting of CREMOPHOR® surfactants and Polysorbate 80.

Also, provided herein is a method of treating a cancer (e.g., any one of cancers described herein), the method comprising the step of administering to a subject in need thereof of a therapeutically effective amount of a pharmaceutical composition comprising a non-covalently bound complex comprising ABOA and human serum albumin as described herein, and a pharmaceutically acceptable carrier. In some embodiments, the method of treating cancer (e.g. any one of cancers described herein) comprises the step of administering to a subject in need thereof a therapeutically effective amount of a pharmaceutical composition a non-covalently bound complex comprising ABOA and human serum albumin as described herein, and a therapeutically effective amount of at least one anti-cancer drug (e.g., any one of anti-cancer agents described herein).

In some embodiments, the cancer is a solid tumor. In some embodiments, the cancer is a prostate cancer. In some embodiments, the cancer is a metastatic castration-resistant prostate cancer.

Compositions Comprising ABOA and Human Serum Albumin

Also, provided herein is a composition comprising ABOA and human serum albumin, wherein the ABOA and the human serum albumin in the composition have a ratio by weight from about 1:1 to about 1:2000.

In some embodiments, the ABOA and the human serum albumin in the composition have a ratio by weight from about 1:5 to about 1:1000, from about 1:10 to about 1:800, from about 1:20 to about 1:600, from about 1:30 to about 1:500, from about 1:30 to about 1:400, from about 1:30 to about 1:300, from about 1:30 to about 1:250, from about 1:30 to about 1:200, from about 1:30 to about 1:150, from about 1:30 to about 1:140, from about 1:30 to about 1:130, from about 1:30 to about 1:120, from about 1:30 to about 1:110, from about 1:30 to about 1:100, from about 1:30 to about 1:90, from about 1:30 to about 1:80, from about 1:30 to about 1:70, from about 1:30 to about 1:60, from about 1:35 to about 1:500, from about 1:35 to about 1:400, from about 1:35 to about 1:300, from about 1:35 to about 1:250, from about 1:35 to about 1:200, from about 1:35 to about 1:150, from about 1:35 to about 1:140, from about 1:35 to about 1:130, from about 1:35 to about 1:120, from about 1:35 to about 1:110, from about 1:35 to about 1:100, from about 1:35 to about 1:90, from about 1:35 to about 1:80, from about 1:35 to about 1:70, from about 1:35 to about 1:60, from about 1:40 to about 1:500, from about 1:40 to about 1:400, from about 1:40 to about 1:300, from about 1:40 to about 1:250, from about 1:40 to about 1:200, from about 1:40 to about 1:150, 1:40 to about 1:140, from about 1:40 to about 1:130, from about 1:40 to about 1:120, from about 1:40 to about 1:110, 1:40 to about 1:100, from about 1:40 to about 1:90, from about 1:40 to about 1:80, from about 1:40 to about 1:70, or from about 1:40 to about 1:60. In some embodiments, the ABOA and the human serum albumin have a ratio by weight of about 1:20, about 1:30, about 1:35, about 1:40, about 1:45, about 1:50, about 1:55, about 1:60, about 1:65, about 1:70, about 1:75, about 1:80, about 1:90, about 1:100, about 1:110, about 1:120, about 1:130, or about 1:140, about 1:150, about 1:160, about 1:170, about 1:180, about 1:190, about 1:200, about 1:210, about 1:220, about 1:230, about 1:240, about 1:250, or about 1:275, about 1:300, about 1:350, about 1:400, about 1:450, or about 1:500.

In some embodiments, the ABOA and the human serum albumin in the composition have a molar ratio from about 50:1 to about 1:10, from about 1:40:1 to about 1:9; from about 30:1 to about 1:8, from about 20:1 to about 1:7, from about 15:1 to about 1:6, from about 12:1 to about 1:5, from about 10:1 to about 1:4, from about 9:1 to about 1:3, from about 8:1 to about 1:2, from about 7:1 to about 1:2, from about 7:1 to about 1:1.5, or from about 6:1 to about 1:1.1. In some embodiments, the ABOA and the human serum albumin in the composition have a molar ratio of about 10:1, about 8:1, about 7:1, about 6:1, about 5.5:1, about 5:1, about 4.8:1, about 4.5:1, about 4.2:1, about 4:1, about 3.8:1, about 3.5:1, about 3:1, about 2.5:1, about 2:1, about 1.9:1, about 1.5:1, about 1.3:1, about 1:1, about 1:1.1, about 1:1.5, about 1:2, about 1:5, or about 1:10.

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free. In some embodiments, the human serum albumin contains no more than two moles of fatty acids bound to one mole of human serum albumin. In some embodiments, the human serum albumin contains no more than one mole of fatty acids bound to one mole of human serum albumin. In some embodiments, human serum albumin contains no more than 0.5 moles of fatty acids bound to one mole of human serum albumin. In some embodiments, the human serum albumin contains no more than 0.1 moles of fatty acids bound to one mole of human serum albumin. In some embodiments, the human serum albumin contains no more than 0.05 moles of fatty acids bound to one mole of human serum albumin. In some embodiments, the human serum albumin contains no more than 0.01 moles of fatty acids bound to one mole of human serum albumin. In some embodiments, the human serum albumin contains no more than 0.001 moles of fatty acids bound to one mole of human serum albumin. In some embodiments, the human serum albumin contains no more than 0.0005 moles of fatty acids bound to one mole of human serum albumin. In some embodiments, the human serum albumin contains no more than 0.0001 moles of fatty acids bound to one mole of human serum albumin.

In some embodiments, the ABOA can be a pharmaceutically acceptable salt of ABOA. In some embodiments, the ABOA is a hydrochloride salt of ABOA. In some embodiments, ABOA can be in crystal forms, amorphous forms, solvates and hydrates.

In some embodiments, the composition is a clear aqueous solution when the composition is dissolved in an aqueous solution. In some embodiments, the aqueous solution is substantially free of solvent other than water. In some embodiments, the aqueous solution is free of solvent other than water.

In some embodiments, the composition is a clear aqueous solution when the composition is dissolved in water. In some embodiments, the composition is a clear aqueous solution when the composition is dissolved in 0.9% saline. In some embodiments, the composition is a clear aqueous solution when the composition is dissolved in 5% Dextrose solution.

As used herein, the term "aqueous solution" refers to a solution, wherein at least one solvent is water and the weight % of water in the mixture of solvents is at least 50%, at least 60%, at least 70% or at least 90%. In some embodiments, aqueous solution is a solution in which water is the only solvent. In some embodiments, aqueous solution is 0.9% saline. In some embodiments, aqueous solution is 5% Dextrose solution. In some embodiments, aqueous solution is a buffer (e.g., phosphate buffer or a carbonate buffer). In some embodiments, the buffer is physiological buffer or a pharmaceutically acceptable buffer. In some embodiments, the buffer is any one of buffers described, for example, in Y.-C. Lee et al. International Journal of Pharmaceutics 253 (2003) 111-119, the disclosure of which is incorporated herein by reference in its entirety. In some embodiments, the buffer comprises maleic acid, tartaric acid, lactic acid, citric acid, acetic acid, sodium bicarbonate, sodium phosphate, or mixtures thereof. In some embodiments, the pH range of the buffer is from about 3 to about 9, from about 4 to about 8, from about 5 to about 7, from about 6.0 to about 6.5, from about 6 to about 7, from about 3 to about 5, from about 3 to about 7, from about 4 to about 6, or from about 5 to about 6. In some embodiments, the pH of the buffer is about 4, about 5, about 6, about 6.1, about 6.2, about 6.3, about 6.4, about 6.5, about 6.6, about 6.7, about 6.8, about 6.9, about 7.0, about 7.5, or about 8.

As used herein, the term "aqueous solvent" refer to a liquid comprising at least 50%, at least 60%, at least 70%, at least 90% or at least 95% water. In some embodiments, aqueous solvent is water, 0.9% saline or 5% dextrose.

As used herein, "substantially free of solvent," in reference to an aqueous solution, refers to an aqueous solution that contains less than 0.5%, by weight, of any non-water solvent. In some embodiments, the aqueous solution contains less than 0.1%, by weight, of any non-water solvent. In some embodiments, the aqueous solution contains less than 0.05%, by weight, of any non-water solvent.

In some embodiments, the term "clear aqueous solution" refers to an aqueous solution containing ABOA and HSA, which is transparent upon visual observation and essentially free of visible particles or precipitation of undissolved ABOA.

The term "essentially free of visible particles or precipitation of undissolved ABOA" can be assessed as follows: after a clear aqueous solution is filtered with a 0.22 micron filter, the amount of ABOA in the filtered aqueous solution is at least 95% of the total amount of ABOA in the aqueous solution before filtration. The total amount of ABOA in the aqueous solution before filtration includes the particles or precipitation of undissolved ABOA in the aqueous solution or with the aqueous solution. The amount of the ABOA in an aqueous solution can be measured by the methods using HPLC. The methods of measuring the amount of the ABOA in an aqueous solution are illustrated in the experimental examples described herein. The methods are commonly understood by one of ordinary skill in the art to which this disclosure belongs.

When visually observed, for example, the term "clear aqueous solution" excludes a milky aqueous solution. Further, the term "clear aqueous solution" excludes a cloudy or hazy aqueous solution.

As used herein, the term "micron" refers to a unit of measure of one one-thousandth of a millimeter. In some embodiments, the term "micron" refers to a micrometer.

In some embodiments, the composition forms a clear aqueous solution, when the composition is dissolved in an aqueous solution, wherein the clear aqueous solution has pH value from about 5 to about 8. In some embodiments, the composition forms a clear aqueous solution, when the composition is dissolved in an aqueous solution, wherein the clear aqueous solution has pH value from about 5.5 to about 7.8. In some embodiments, the composition forms a clear aqueous solution, when the composition is dissolved in an aqueous solution, wherein the clear aqueous solution has pH value from about 6 to about 7.5. In some embodiments, the composition forms a clear aqueous solution, when the composition is dissolved in an aqueous solution, wherein the clear aqueous solution has pH value from about 6.5 to about 7.5. In some embodiments, the composition forms a clear aqueous solution, when the composition is dissolved in an aqueous solution, wherein the clear aqueous solution has pH value from about 6 to about 6.5. In some embodiments, the composition forms a clear aqueous solution, when the composition is dissolved in an aqueous solution, wherein the clear aqueous solution has pH value from about 6.5 to about 7. In some embodiments, the composition forms a clear aqueous solution, when the composition is dissolved in an aqueous solution, wherein the clear aqueous solution has pH value from about 7 to about 7.5. In some embodiments, the composition forms a clear aqueous solution, when the composition is dissolved in an aqueous solution, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous solution is substantially free of solvent other than water. In some embodiments, the aqueous solution is free of solvent other than water.

In some embodiments, the composition forms a clear aqueous solution, when the composition is dissolved in water, wherein the clear aqueous solution has pH value from about 5 to about 8. In some embodiments, the composition forms a clear aqueous solution, when the composition is dissolved in water, wherein the clear aqueous solution has pH value from about 5.5 to about 7.8. In some embodiments, the composition forms a clear aqueous solution, when the composition is dissolved in water, wherein the clear aqueous solution has pH value from about 6 to about 7.5. In some embodiments, the composition forms a clear aqueous solution, when the composition is dissolved in water, wherein the clear aqueous solution has pH value from about 6.5 to about 7.5. In some embodiments, the composition forms a clear aqueous solution, when the composition is dissolved in water, wherein the clear aqueous solution has pH value from about 6 to about 6.5. In some embodiments, the composition forms a clear aqueous solution, when the composition is dissolved in water, wherein the clear aqueous solution has pH value from about 6.5 to about 7. In some embodiments, the composition forms a clear aqueous solution, when the composition is dissolved in water, wherein the clear aqueous solution has pH value from about 7 to about 7.5. In some embodiments, the composition forms a clear aqueous solution, when the composition is dissolved in water, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

In some embodiments, the composition forms a clear aqueous solution, when the composition is dissolved in 0.9% saline, wherein the clear aqueous solution has pH value from about 5 to about 8. In some embodiments, the composition forms a clear aqueous solution, when the composition is dissolved in 0.9% saline, wherein the clear aqueous solution has pH value from about 5.5 to about 7.8. In some embodiments, the composition forms a clear aqueous solution, when the composition is dissolved in 0.9% saline, wherein the clear aqueous solution has pH value from about 6 to about 7.5. In some embodiments, the composition forms a clear aqueous solution, when the composition is dissolved in 0.9% saline, wherein the clear aqueous solution has pH value from about 6.5 to about 7.5. In some embodiments, the composition forms a clear aqueous solution, when the composition is dissolved in 0.9% saline, wherein the clear aqueous solution has pH value from about 6 to about 6.5. In some embodiments, the composition forms a clear aqueous solution, when the composition is dissolved in 0.9% saline, wherein the clear aqueous solution has pH value from about 6.5 to about 7. In some embodiments, the composition forms a clear aqueous solution, when the composition is dissolved in 0.9% saline, wherein the clear aqueous solution has pH value from about 7 to about 7.5. In some embodiments, the composition forms a clear aqueous solution, when the composition is dissolved in 0.9% saline, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

In some embodiments, the composition forms a clear aqueous solution, when the composition is dissolved in 5% Dextrose solution, wherein the clear aqueous solution has pH value from about 5 to about 8. In some embodiments, the composition forms a clear aqueous solution, when the composition is dissolved in 5% Dextrose solution, wherein the clear aqueous solution has pH value from about 5.5 to about 7.8. In some embodiments, the composition forms a clear aqueous solution, when the composition is dissolved in 5% Dextrose solution, wherein the clear aqueous solution has pH value from about 6 to about 7.5. In some embodiments, the composition forms a clear aqueous solution, when the composition is dissolved in 5% Dextrose solution, wherein the clear aqueous solution has pH value from about 6.5 to about 7.5. In some embodiments, the composition forms a clear aqueous solution, when the composition is dissolved in 5% Dextrose solution, wherein the clear aqueous solution has pH value from about 6 to about 6.5. In some embodiments, the composition forms a clear aqueous solution, when the composition is dissolved in 5% Dextrose solution, wherein the clear aqueous solution has pH value from about 6.5 to about 7. In some embodiments, the composition forms a clear aqueous solution, when the composition is dissolved in 5% Dextrose solution, wherein the clear aqueous solution has pH value from about 7 to about 7.5. In some embodiments, the composition forms a clear aqueous solution, when the composition is dissolved in 5% Dextrose solution, wherein the clear aqueous solution has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

In some embodiments, when the composition comprising ABOA and human serum albumin as described herein (e.g., sterile solid powder) is dissolved in an aqueous solvent (e.g., water, 0.9% saline or 5% dextrose), the resultant aqueous solution, when filtered using a 0.22 micron filter, comprises 100% at the time of preparation, at least 98.7% after 1 hour, at least 98.7% after 2 hours, at least 98.2% after 3 hours, at least 98.2% after 4 hours, at least 98.2% after 5 hours, or at least 98.2% after 6 hours of the amount of ABOA used to prepare the composition.

In some embodiments, when the composition comprising ABOA and human serum albumin as described herein (e.g., sterile solid powder) is dissolved in an aqueous solvent (e.g., water, 0.9% saline or 5% dextrose), the resultant aqueous solution, when filtered using a 0.22 micron filter, comprises 99% at the time of preparation, at least 99% after 1 hour, at least 99% after 2 hours, at least 99% after 3 hours, at least 99% after 4 hours, at least 99% after 5 hours, or at least 99% after 6 hours of the amount of ABOA used to prepare the composition.

In some embodiments, when the composition comprising ABOA and human serum albumin as described herein (e.g., sterile solid powder) is dissolved in an aqueous solvent (e.g., water, 0.9% saline or 5% dextrose), the resultant aqueous solution, when filtered using a 0.22 micron filter, comprises 98% at the time of preparation, at least 98% after 1 hour, at least 98% after 2 hours, at least 98% after 3 hours, at least 98% after 4 hours, at least 98% after 5 hours, at least 98% after 6 hours, or at least 98% after 24 hours of the amount of ABOA used to prepare the composition.

In some embodiments, when the composition comprising ABOA and human serum albumin as described herein (e.g., sterile solid powder) is dissolved in an aqueous solvent (e.g., water, 0.9% saline or 5% dextrose), the resultant aqueous solution, when filtered using a 0.22 micron filter, comprises 97% at the time of preparation, at least 97% after 1 hour, at least 97% after 2 hours, at least 97% after 3 hours, at least 97% after 4 hours, at least 97% after 5 hours, at least 97% after 6 hours, or at least 97% after 24 hours of the amount of ABOA used to prepare the composition.

In some embodiments, when the composition comprising ABOA and human serum albumin as described herein (e.g., sterile solid powder) is dissolved in an aqueous solvent (e.g., water, 0.9% saline or 5% dextrose), the resultant aqueous solution, when filtered using a 0.22 micron filter, comprises 96% at the time of preparation, at least 96% after 1 hour, at least 96% after 2 hours, at least 96% after 3 hours, at least 96% after 4 hours, at least 96% after 5 hours, at least 96% after 6 hours, or at least 96% after 24 hours of the amount of ABOA used to prepare the composition.

In some embodiments, when the composition comprising ABOA and human serum albumin as described herein (e.g., sterile solid powder) is dissolved in an aqueous solvent (e.g., water, 0.9% saline or 5% dextrose), the resultant aqueous solution, when filtered using a 0.22 micron filter, comprises 95% at the time of preparation, at least 95% after 1 hour, at least 95% after 2 hours, at least 95% after 3 hours, at least 95% after 4 hours, at least 95% after 5 hours, at least 95% after 6 hours, or at least 95% after 24 hours of the amount of ABOA used to prepare the composition.

In some embodiments, the composition is a clear aqueous solution when the composition is dissolved in an aqueous solvent (e.g., Water, 0.9% saline, or 5% Dextrose solution), wherein after the clear aqueous solution is filtered by a 0.22 micron filter after a time period selected from 1 hour, 2 hours, 3 hours, 4 hours, 5 hours, 6 hours and 24 hours, the amount of ABOA in the filtered aqueous solution is at least 96% of the total amount of ABOA in the aqueous solution at the time of dissolution before the filtration. In some embodiments, the composition is a clear aqueous solution when the composition is dissolved in an aqueous solvent (e.g., Water, 0.9% saline, or 5% Dextrose solution), wherein after the clear aqueous solution is filtered by a 0.22 micron filter after a time period selected from 1 hour, 2 hours, 3 hours, 4 hours, 5 hours, 6 hours and 24 hours, the amount of ABOA in the filtered aqueous solution is at least 97% of the total amount of ABOA in the aqueous solution at the time of dissolution before the filtration. In some embodiments, the composition is a clear aqueous solution when the composition is dissolved in an aqueous solvent (e.g., Water, 0.9% saline, or 5% Dextrose solution), wherein after the clear aqueous solution is filtered by a 0.22 micron filter after a time period selected from 1 hour, 2 hours, 3 hours, 4 hours, 5 hours, 6 hours and 24 hours, the amount of ABOA in the filtered aqueous solution is at least 98% of the total amount of ABOA in the aqueous solution at the time of dissolution before the filtration. In some embodiments, the composition is a clear aqueous solution when the composition is dissolved in an aqueous solvent (e.g., Water, 0.9% saline, or 5% Dextrose solution), wherein after the clear aqueous solution is filtered by a 0.22 micron filter after a time period selected from 1 hour, 2 hours, 3 hours, 4 hours, 5 hours, 6 hours and 24 hours, the amount of ABOA in the filtered aqueous solution is at least 99% of the total amount of ABOA in the aqueous solution at the time of dissolution before the filtration. In some embodiments, the composition is a clear aqueous solution when the composition is dissolved in an aqueous solvent (e.g., Water, 0.9% saline, or 5% Dextrose solution), wherein after the clear aqueous solution is filtered by a 0.22 micron filter after a time period selected from 1 hour, 2 hours, 3 hours, 4 hours, 5 hours, 6 hours and 24 hours, the amount of ABOA in the filtered aqueous solution is at least 99.5% of the total amount of ABOA in the aqueous solution at the time of dissolution before the filtration. In some embodiments, the aqueous solution is free of solvent other than water. In some embodiments, the aqueous solution is substantially free of solvent other than water.

In some embodiments, the amount of ABOA that is bound to the HSA (e.g., non-covalently) in the aqueous solution (e.g., clear aqueous solution) comprising the composition comprising ABOA and HSA (as described herein) is at least 40%, at least 50%, at least 60%, at least 70%, at least 80%, at least 90%, at least 95%, at least 99%, or about 100% of the total about of ABOA in the aqueous solution.

In some embodiments, the composition is a clear aqueous solution when the composition is dissolved in an aqueous solvent (e.g., Water, 0.9% saline, or 5% Dextrose solution), wherein after the clear aqueous solution is filtered by a 0.22 micron filter after a time period selected from 1 hour, 2 hours, 3 hours, 4 hours, 5 hours, 6 hours and 24 hours, the amount of ABOA in the filtered aqueous solution is at least 96%, 97%, 98%, 99%, or 99.5% of the total amount of ABOA in the aqueous solution at the time of dissolution before the filtration, wherein the clear aqueous solution has pH value from about 5 to about 8, from about 5.5 to about 7.5, from about 6 to about 7, or from about 6 to about 6.5. In some embodiments, the composition is a clear aqueous solution when the composition is dissolved in an aqueous aqueous solvent (e.g., Water, 0.9% saline, or 5% Dextrose solution), wherein after the clear aqueous solution is filtered by a 0.22 micron filter after a time period selected from 1 hour, 2 hours, 3 hours, 4 hours, 5 hours, 6 hours and 24 hours, the amount of ABOA in the filtered aqueous solution is at least 96%, 97%, 98%, 99%, or 99.5% of the total amount of ABOA in the aqueous solution at the time of dissolution before the filtration, wherein the clear aqueous solution has pH value from about 6 to about 7.5.

In some embodiments, the composition is an aqueous solution, wherein after the aqueous solution is filtered by a 0.22 micron filter, the amount of ABOA in the filtered aqueous solution is at least 80% of the total amount of ABOA in the aqueous solution before the filtration. In some embodiments, the composition is an aqueous solution, wherein after the aqueous solution is filtered by a 0.22 micron filter, the amount of ABOA in the filtered aqueous solution is at least 85% of the total amount of ABOA in the aqueous solution before the filtration. In some embodiments, the composition is an aqueous solution, wherein after the aqueous solution is filtered by a 0.22 micron filter, the amount of ABOA in the filtered aqueous solution is at least 90% of the total amount of ABOA in the aqueous solution before the filtration. In some embodiments, the composition is an aqueous solution, wherein after the aqueous solution is filtered by a 0.22 micron filter, the amount of ABOA in the filtered aqueous solution is at least 95% of the total amount of ABOA in the aqueous solution before the filtration. In some embodiments, the composition is an aqueous solution, wherein after the aqueous solution is filtered by a 0.22 micron filter, the amount of ABOA in the filtered aqueous solution is at least 98% of the total amount of ABOA in the aqueous solution before the filtration. In some embodiments, the composition is an aqueous solution, wherein after the aqueous solution is filtered by a 0.22 micron filter, the amount of ABOA in the filtered aqueous solution is at least 99% of the total amount of ABOA in the aqueous solution before the filtration. In some embodiments, the composition is an aqueous solution, wherein after the aqueous solution is filtered by a 0.22 micron filter, the amount of ABOA in the filtered aqueous solution is 100% of the total amount of ABOA in the aqueous solution before the filtration. In some embodiments, the aqueous solution is free of solvent other than water. In some embodiments, the aqueous solution is substantially free of solvent other than water.

In some embodiments, the composition is a clear aqueous solution for at least 1 hour when the composition is dissolved in an aqueous solution. In some embodiments, the composition is a clear aqueous solution for at least 2 hours when the composition is dissolved in an aqueous solution. In some embodiments, the composition is a clear aqueous solution for at least 3 hours when the composition is dissolved in an aqueous solution. In some embodiments, the composition is a clear aqueous solution for at least 4 hours when the composition is dissolved in an aqueous solution. In some embodiments, the composition is a clear aqueous solution for at least 5 hours when the composition is dissolved in an aqueous solution. In some embodiments, the composition is a clear aqueous solution for at least 6 hours when the composition is dissolved in an aqueous solution. In some embodiments, the composition is a clear aqueous solution for at least 8 hours when the composition is dissolved in an aqueous solution. In some embodiments, the composition is a clear aqueous solution for at least 24 hours when the composition is dissolved in an aqueous solution. In some embodiments, the aqueous solution is substantially free of solvent other than water. In some embodiments, the aqueous solution free of solvent other than water.

In some embodiments, the composition is a solid formulation. For example, the solid formulation can be produced in a uniform manner by lyophilization. A skilled artisan would recognize other methods, such as rotary evaporation, that can also produce solid formulations.

In some embodiments, the composition is an aqueous formulation. In some embodiments, the aqueous formulation is substantially free of solvent other than water. In some embodiments, the aqueous formulation is free of solvent other than water.

In some embodiments, the aqueous formulation can be free of a surfactant, such as CREMOPHOR® surfactants and Polysorbate 80. In some embodiments, the aqueous formulation can be substantially free of a surfactant, such as CREMOPHOR® surfactants and Polysorbate 80. In some embodiments, the aqueous formulation can be substantially free of a surfactant selected from the group consisting of CREMOPHOR® surfactants and Polysorbate 80.

As used herein, the term "substantially free of surfactant" refers to a formulation containing less than 0.0005%, less than 0.0003%, or less than 0.0001% of surfactants and/or less than 0.0005%, less than 0.0003%, or less than 0.0001% of surfactant.

In some embodiments, the aqueous formulation is a clear aqueous solution. For example, the formulation can be a clear and stable aqueous solution reconstituted from a sterile lyophilized powder. In some embodiments, the aqueous formulation is a clear aqueous solution, wherein the aqueous formulation is substantially free of solvent other than water. In some embodiments, the aqueous formulation is a clear aqueous solution, wherein the aqueous formulation is free of solvent other than water.

In some embodiments, the aqueous formulation is a clear aqueous solution reconstituted from the solid formulation (e.g. the sterile lyophilized powder) in water. In some embodiments, the aqueous formulation is a clear aqueous solution reconstituted from the solid formulation (e.g. the sterile lyophilized powder) in 0.9% saline. In some embodiments, the aqueous formulation is a clear aqueous solution reconstituted from the solid formulation (e.g. the sterile lyophilized powder) in 5% Dextrose solution.

In some embodiments, the aqueous formulation is a clear aqueous solution reconstituted from the solid formulation (e.g. the sterile lyophilized powder) in water, wherein the aqueous formulation has pH value from about 5 to about 8. In some embodiments, the aqueous formulation is a clear aqueous solution reconstituted from the solid formulation (e.g. the sterile lyophilized powder) in 0.9% saline, wherein the aqueous formulation has pH value from about 5 to about 8. In some embodiments, the aqueous formulation is a clear aqueous solution reconstituted from the solid formulation (e.g. the sterile lyophilized powder) in 5% Dextrose solution, wherein the aqueous formulation has pH value from about 5 to about 8.

In some embodiments, the aqueous formulation is a clear aqueous solution reconstituted from the solid formulation (e.g. the sterile lyophilized powder) in water, wherein the aqueous formulation has pH value from about 6 to about 7.5. In some embodiments, the aqueous formulation is a clear aqueous solution reconstituted from the solid formulation (e.g. the sterile lyophilized powder) in 0.9% saline, wherein the aqueous formulation has pH value from about 6 to about 7.5. In some embodiments, the aqueous formulation is a clear aqueous solution reconstituted from the solid formulation (e.g. the sterile lyophilized powder) in 5% Dextrose solution, wherein the aqueous formulation has pH value from about 6 to about 7.5.

In some embodiments, the aqueous formulation has pH value from about 5 to about 8. In some embodiments, the aqueous formulation has pH value from about 5.5 to about 7.8. In some embodiments, the aqueous formulation has pH value from about 6 to about 7.5. In some embodiments, the aqueous formulation has pH value from about 6.5 to about 7.5. In some embodiments, the aqueous formulation has pH value from about 6 to about 6.5. In some embodiments, the aqueous formulation has pH value from about 6.5 to about 7. In some embodiments, the aqueous formulation has pH value from about 7 to about 7.5. In some embodiments, the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous formulation is substantially free of solvent other than water. In some embodiments, the aqueous formulation is free of solvent other than water.

In some embodiments, the aqueous formulation is a clear aqueous solution, wherein the aqueous formulation has pH value from about 5 to about 8, and wherein the aqueous formulation is substantially free of solvent other than water. In some embodiments, the aqueous formulation is a clear aqueous solution, wherein the aqueous formulation has pH value from about 5 to about 8, and wherein the aqueous formulation is free of solvent other than water. In some embodiments, the aqueous formulation is a clear aqueous solution, wherein the aqueous formulation has pH value from about 5.5 to about 7.8, and wherein the aqueous formulation is substantially free of solvent other than water. In some embodiments, the aqueous formulation is a clear aqueous solution, wherein the aqueous formulation has pH value from about 5.5 to about 7.8, and wherein the aqueous formulation is free of solvent other than water. In some embodiments, the aqueous formulation is a clear aqueous solution, wherein the aqueous formulation has pH value from about 6 to about 7.5, and wherein the aqueous formulation is substantially free of solvent other than water. In some embodiments, the aqueous formulation is a clear aqueous solution, wherein the aqueous formulation has pH value from about 6 to about 7.5, and wherein the aqueous formulation is free of solvent other than water. In some embodiments, the aqueous formulation is a clear aqueous solution, wherein the aqueous formulation has pH value from about 6.5 to about 7.5, and wherein the aqueous formulation is substantially free of solvent other than water. In some embodiments, the aqueous formulation is a clear aqueous solution, wherein the aqueous formulation has pH value from about 6.5 to about 7.5, and wherein the aqueous formulation is free of solvent other than water. In some embodiments, the aqueous formulation is a clear aqueous solution, wherein the aqueous formulation has pH value from about 6 to about 6.5, and wherein the aqueous formulation is substantially free of solvent other than water. In some embodiments, the aqueous formulation is a clear aqueous solution, wherein the aqueous formulation has pH value from about 6 to about 6.5, and wherein the aqueous formulation is free of solvent other than water. In some embodiments, the aqueous formulation is a clear aqueous solution, wherein the aqueous formulation has pH value from about 6.5 to about 7, and wherein the aqueous formulation is substantially free of solvent other than water. In some embodiments, the aqueous formulation is a clear aqueous solution, wherein the aqueous formulation has pH value from about 6.5 to about 7, and wherein the aqueous formulation is free of solvent other than water. In some embodiments, the aqueous formulation is a clear aqueous solution, wherein the aqueous formulation has pH value from about 7 to about 7.5, and wherein the aqueous formulation is substantially free of solvent other than water. In some embodiments, the aqueous formulation is a clear aqueous solution, wherein the aqueous formulation has pH value from about 7 to about 7.5, and wherein the aqueous formulation is free of solvent other than water. In some embodiments, the aqueous formulation is a clear aqueous solution, wherein the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5, and wherein the aqueous formulation is substantially free of solvent other than water. In some embodiments, the aqueous formulation is a clear aqueous solution, wherein the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5, and wherein the aqueous formulation is free of solvent other than water.

In some embodiments, the aqueous formulation is a clear aqueous solution for at least 1 hour. In some embodiments, the aqueous formulation is a clear aqueous solution for at least 1 hour at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 2 hours. In some embodiments, the aqueous formulation is a clear aqueous solution for at least 2 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 3 hours. In some embodiments, the aqueous formulation is a clear aqueous solution for at least 3 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 6 hours. In some embodiments, the aqueous formulation is a clear aqueous solution for at least 6 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 24 hours. In some embodiments, the aqueous formulation is a clear aqueous solution for at least 24 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 3 days. In some embodiments, the aqueous formulation is a clear aqueous solution for at least 3 days when dissolved in an aqueous solution at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least about 1 hour, 2 hours, 3 hours, 4 hours, 5 hours, 6 hours, 8 hours, or 24 hours. In some embodiments, the aqueous formulation is substantially free of solvent other than water. In some embodiments, the aqueous formulation is free of solvent other than water.

In some embodiments, after the aqueous formulation (e.g. a clear aqueous solution) is filtered by a 0.22 micron filter, the amount of ABOA in the filtered aqueous solution is at least 96% of the total amount of ABOA in the aqueous solution before the filtration. In some embodiments, after the aqueous formulation (e.g. a clear aqueous solution) is filtered by a 0.22 micron filter, the amount of ABOA in the filtered aqueous solution is at least 97% of the total amount of ABOA in the aqueous solution before the filtration. In some embodiments, after the aqueous formulation (e.g. a clear aqueous solution) is filtered by a 0.22 micron filter, the amount of ABOA in the filtered aqueous solution is at least 98% of the total amount of ABOA in the aqueous solution before the filtration. In some embodiments, after the aqueous formulation (e.g. a clear aqueous solution) is filtered by a 0.22 micron filter, the amount of ABOA in the filtered aqueous solution is at least 99% of the total amount of ABOA in the aqueous solution before the filtration. In some embodiments, after the aqueous formulation (e.g. a clear aqueous solution) is filtered by a 0.22 micron filter, the amount of ABOA in the filtered aqueous solution is at least 99.5% of the total amount of ABOA in the aqueous solution before the filtration. In some aspects of these embodiments, the aqueous formulation is filtered by a 0.22-micron filter at a time period selected from 1 hour, 2 hours, 3, hours, 4 hours, 5 hours, 6 hours, 12 hours, 18 hours and 24 hours. In some embodiments, the aqueous formulation is free of solvent other than water. In some embodiments, the aqueous formulation is substantially free of solvent other than water.

In some embodiments, after the aqueous formulation (e.g. a clear aqueous solution) is filtered by a 0.22 micron filter, the amount of ABOA in the filtered aqueous solution is at least 95%, 96%, 97%, 98%, 99%, or 99.5% of the total amount of ABOA in the aqueous solution before filtration, wherein the clear aqueous solution has pH value from about 5 to about 8, and wherein the clear aqueous solution is substantially free of solvent other than water. In some embodiments, after the aqueous formulation (e.g. a clear aqueous solution) is filtered by a 0.22 micron filter, the amount of ABOA in the filtered aqueous solution is at least 95%, 96%, 97%, 98%, 99%, or 99.5% of the total amount of ABOA in the aqueous solution before filtration, wherein the clear aqueous solution has pH value from about 6 to about 7.5, and wherein the clear aqueous solution is substantially free of solvent other than water. In some embodiments, after the aqueous formulation (e.g. a clear aqueous solution) is filtered by a 0.22 micron filter, the amount of ABOA in the filtered aqueous solution is at least 95%, 96%, 97%, 98%, 99%, or 99.5% of the total amount of ABOA in the aqueous solution before filtration, wherein the clear aqueous solution has pH value from about 5 to about 8, and wherein the clear aqueous solution is free of solvent other than water. In some embodiments, after the aqueous formulation (e.g. a clear aqueous solution) is filtered by a 0.22 micron filter, the amount of ABOA in the filtered aqueous solution is at least 95%, 96%, 97%, 98%, 99%, or 99.5% of the total amount of ABOA in the aqueous solution before filtration, wherein the clear aqueous solution has pH value from about 6 to about 7.5, and wherein the clear aqueous solution is free of solvent other than water. In some aspects of these embodiments, the aqueous formulation is filtered by a 0.22-micron filter at a time period selected from 1 hour, 2 hours, 3, hours, 4 hours, 5 hours, 6 hours, 12 hours, 18 hours and 24 hours.

In some embodiments, after the aqueous formulation is filtered by a 0.22 micron filter, the amount of ABOA in the filtered aqueous solution is at least 80% of the total amount of ABOA in the aqueous solution before the filtration. In some embodiments, after the aqueous formulation is filtered by a 0.22 micron filter, the amount of ABOA in the filtered aqueous solution is at least 85% of the total amount of ABOA in the aqueous solution before the filtration. In some embodiments, after the aqueous formulation is filtered by a 0.22 micron filter, the amount of ABOA in the filtered aqueous solution is at least 90% of the total amount of ABOA in the aqueous solution before the filtration. In some aspects of these embodiments, the aqueous formulation is filtered by a 0.22-micron filter at a time period selected from 1 hour, 2 hours, 3, hours, 4 hours, 5 hours, 6 hours, 12 hours, 18 hours and 24 hours. In some embodiments, the aqueous formulation is free of solvent other than water. In some embodiments, the aqueous formulation is substantially free of solvent other than water.

Also, provided herein is a pharmaceutical composition comprising the composition comprising the ABOA and the human serum albumin as described herein, and a pharmaceutically acceptable carrier.

In some embodiments, the pharmaceutical composition further comprises at least one anti-cancer drug (e.g., any one of the anti-cancer drugs as described herein).

As used herein, the term "pharmaceutically acceptable carrier" is meant any solution used to solubilize and deliver an agent to a subject. A desirable pharmaceutically acceptable carrier is saline. Other pharmaceutically acceptable carrier and their formulation are known to one skilled in the art and described, for example, in Remington's Pharmaceutical Sciences. (20$^{th}$ edition), ed. A. Gennaro, 2003, Lippincon Williams & Wilkins.

Pharmaceutically acceptable carriers that may be used in the pharmaceutical compositions of the present application include, but are not limited to, ion exchangers, alumina, aluminum stearate, lecithin, serum proteins (other than HSA), buffer substances such as phosphates, glycine, sorbic acid, potassium sorbate, salts or electrolytes, such as protamine sulfate, disodium hydrogen phosphate, potassium hydrogen phosphate, sodium chloride, zinc salts, colloidal silica, magnesium tri silicate, and cellulose-based substances.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use.

Extemporaneous injection solutions and suspensions can be prepared from sterile powders, granules, and tablets.

In some embodiments, the pharmaceutical composition is free of a surfactant, such as CREMOPHOR® surfactants and Polysorbate 80. In some embodiments, the pharmaceutical composition is substantially free of a surfactant, such as CREMOPHOR® surfactants and Polysorbate 80. In some embodiments, the pharmaceutical composition can be substantially free of a surfactant selected from the group consisting of CREMOPHOR® surfactants and Polysorbate 80.

Also, provided herein is a method of treating a proliferative disease comprising the step of administering to a subject in need thereof a pharmaceutical composition comprising the composition comprising the ABOA and the human serum albumin as described herein, and a pharmaceutically acceptable carrier.

As used herein, the terms "individual", "patient", or "subject" are used interchangeably and refer to any animal, including mammals, preferably mice, rats, other rodents, rabbits, dogs, cats, swine, cattle, sheep, horses, or primates, and most preferably humans.

As used herein, the term "proliferative disease" refers to a disease caused by excessive proliferation of cells and turnover of cellular matrix. Non-limiting examples of proliferative diseases include cancer, atherosclerosis, arthritis (e.g. rheumatoid arthritis), psoriasis, fibrosis (e.g. pulmonary fibrosis, idiopathic pulmonary fibrosis), scleroderma and cirrhosis (e.g. cirrhosis of the liver).

Also, provided herein is a method of treating a cancer (e.g., any one of cancers described herein), the method comprising the step of administering to a subject in need thereof of a therapeutically effective amount of a pharmaceutical composition comprising the composition comprising the ABOA and the human serum albumin as described herein, and a pharmaceutically acceptable carrier.

As used herein the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

In some embodiments, cancer is selected from sarcoma, angiosarcoma, fibrosarcoma, rhabdomyosarcoma, liposarcoma, myxoma, rhabdomyoma, fibroma, lipoma, teratoma, non-small cell lung cancer (NSCLC), bronchogenic carcinoma squamous cell, undifferentiated small cell, undifferentiated large cell, adenocarcinoma, alveolar bronchiolar carcinoma, bronchial adenoma, sarcoma, lymphoma, chondromatous hamartoma, mesothelioma, gastrointestinal cancer, cancer of the esophagus, squamous cell carcinoma, adenocarcinoma, leiomyosarcoma, lymphoma, cancer of the stomach, carcinoma, lymphoma, leiomyosarcoma, cancer of the pancreas, ductal adenocarcinoma, insulinoma, glucagonoma, gastrinoma, carcinoid tumor, vipoma, cancer of the small bowel, adenocarcinoma, lymphoma, carcinoid tumors, Kaposi's sarcoma, leiomyoma, hemangioma, lipoma, neurofibroma, fibroma, cancer of the large bowel or colon, tubular adenoma, villous adenoma, hamartoma, leiomyoma, genitourinary tract cancer, cancer of the kidney adenocarcinoma, Wilm's tumor (nephroblastoma), lymphoma, leukemia, cancer of the bladder, cancer of the urethra, squamous cell carcinoma, transitional cell carcinoma, cancer of the prostate, cancer of the testis, seminoma, teratoma, embryonal carcinoma, teratocarcinoma, choriocarcinoma, sarcoma, interstitial cell carcinoma, fibroma, fibroadenoma, adenomatoid tumors, lipoma, liver cancer, hepatoma hepatocellular carcinoma, cholangiocarcinoma, hepatoblastoma, angiosarcoma, hepatocellular adenoma, hemangioma, bone cancer, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochrondroma (osteocartilaginous exostoses), benign chondroma, chondroblastoma, chondromyxofibroma, osteoid osteoma giant cell tumor, nervous system cancer, cancer of the skull, osteoma, hemangioma, granuloma, xanthoma, osteitis deformans, cancer of the meninges meningioma, meningiosarcoma, gliomatosis, cancer of the brain, astrocytoma, medulloblastoma, glioma, ependymoma, germinoma (pinealoma), glioblastoma multiforme, oligodendroglioma, schwannoma, retinoblastoma, congenital tumors, cancer of the spinal cord, neurofibroma, meningioma, glioma, sarcoma, gynecological cancer, cancer of the uterus, endometrial carcinoma, cancer of the cervix, cervical carcinoma, pre tumor cervical dysplasia, cancer of the ovaries, ovarian carcinoma, serous cystadenocarcinoma, mucinous cystadenocarcinoma, unclassified carcinoma, granulosa-theca cell tumor, Sertoli Leydig cell tumor, dysgerminoma, malignant teratoma, cancer of the vulva, squamous cell carcinoma, intraepithelial carcinoma, adenocarcinoma, fibrosarcoma, melanoma, cancer of the vagina, clear cell carcinoma, squamous cell carcinoma, botryoid sarcoma, embryonal rhabdomyosarcoma, cancer of the fallopian tubes, hematologic cancer, cancer of the blood, acute myeloid leukemia (AML), chronic myeloid leukemia (CIVIL), acute lymphoblastic leukemia (ALL), chronic lymphoblastic leukemia, chronic lymphocytic leukemia, myeloproliferative diseases, multiple myeloma, myelodysplastic syndrome, Hodgkin's lymphoma, non-Hodgkin's lymphoma (malignant lymphoma), Waldenstrom's macroglobulinemia, skin cancer, malignant melanoma, basal cell carcinoma, squamous cell carcinoma, Kaposi's sarcoma, moles dysplastic nevi, lipoma, angioma, dermatofibroma, keloids, psoriasis, adrenal gland cancer, and neuroblastoma.

As used herein, an "effective amount," "therapeutically effective amount," or a "pharmaceutically-effective amount" in reference to the compounds or compositions of the instant invention refers to the amount sufficient to induce a desired biological, pharmacological, or therapeutic outcome in a subject. That result can be reduction, mitigation, delay, shortening the time to resolution of, alleviation of the signs or symptoms of, or exert a medically-beneficial effect upon the underlying pathophysiology or pathogenesis of an expected or observed side-effect, toxicity, disorder or condition, or any other desired alteration of a biological system. In cancer treatment, the result will generally include the reduction, mitigation, limitation, and/or, delay of the deleterious physiological manifestations, growth or metastases of neoplasms.

In some embodiments, the cancer is a solid tumor. In some embodiments, the cancer is a prostate cancer. In some embodiments, the cancer is a metastatic castration-resistant prostate cancer.

In some embodiments, the method of treating cancer (e.g., any one of cancers described herein) comprises the step of administering to a subject in need thereof a therapeutically effective amount of a pharmaceutical composition comprising the composition comprising the ABOA and the human serum albumin as described herein, and a therapeutically effective amount of at least one inhibitor of the following kinases for the treatment of cancer: PIM, Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFaR, PDGFl3R, CSFlR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf.

In some embodiments, the method of treating cancer (e.g. any one of cancers described herein) comprises the step of administering to a subject in need thereof a therapeutically effective amount of a pharmaceutical composition comprising the composition comprising the ABOA and the human serum albumin as described herein, and a therapeutically effective amount of at least one anti-cancer drug. Examples of an anti-cancer drug include aberaterone, aberaterone acetate, abarelix, aldesleukin, alemtuzumab, alitretinoin, allopurinol, altretamine, anastrozole, arsenic trioxide, asparaginase, azacitidine, bavituximab, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, enzalutamide, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

In some embodiments, the method of treating cancer (e.g., any one of cancers described herein) comprises the step of administering to a subject in need thereof a therapeutically effective amount of a pharmaceutical composition comprising the composition comprising the ABOA and the human serum albumin as described herein, and a therapeutically effective amount of prednisone.

In some embodiments, the method of treating cancer in a subject (e.g., any one of cancers described herein) comprises the step of administering to the subject in need thereof a therapeutically effective amount of a non-covalently bound complex comprising ABOA and the human serum albumin (e.g., as described herein), and a therapeutically effective amount of prednisone.

In some embodiments, the composition comprising the ABOA and the HSA, and prednisone may be administered to the subject simultaneously. In some embodiments, the composition comprising the ABOA and the HSA, and prednisone may be administered to the subject consecutively.

In some embodiments, the non-covalently bound complex comprising ABOA and the HSA and prednisone may be administered to the subject simultaneously. In some embodiments, the non-covalently bound complex comprising ABOA and the HSA, and prednisone may be administered to the subject consecutively.

In some embodiments, the present application provides a pharmaceutical composition comprising a composition comprising the ABOA and the HSA (e.g., as described herein), prednisone, and a pharmaceutically acceptable carrier.

In some embodiments, the present application provides a pharmaceutical composition comprising a the non-covalently bound complex comprising ABOA and the HSA (e.g., as described herein), prednisone, and a pharmaceutically acceptable carrier.

In some embodiments, the method of treating prostate cancer comprises the step of administering to a subject in need thereof a therapeutically effective amount of a pharmaceutical composition comprising the composition comprising the ABOA and the human serum albumin as described herein, and a therapeutically effective amount of prednisone.

In some embodiments, the method of treating metastatic castration-resistant prostate cancer comprises the step of administering to a subject in need thereof a therapeutically effective amount of a pharmaceutical composition comprising the composition comprising the ABOA and the human serum albumin as described herein, and a therapeutically effective amount of prednisone.

In some embodiments, a composition comprising the ABOA and the human serum albumin as described herein and an anti-cancer drug are administered simultaneously.

In some embodiments, a composition comprising the ABOA and the human serum albumin as described herein and an anti-cancer drug are administered consecutively.

The composition comprising the ABOA and the human serum albumin described herein can be administered to an individual, such as human, via various routes, such as parenterally, including intravenous (e.g., as an infusion), intra-arterial, intraperitoneal, intrapulmonary, oral, inhalation, intravesicular, intramuscular, intra-tracheal, subcutaneous, intraocular, intrathecal, or transdermal. For example, the composition can be administered by inhalation to treat conditions of the respiratory tract. The composition can be used to treat respiratory conditions such as pulmonary fibrosis, broncheolitis obliterans, lung cancer, bronchoalveolar carcinoma, and the like. In some embodiments, the composition is administrated intravenously.

The methods described herein may be performed alone or in conjunction with another therapy, such as surgery, radiation, chemotherapy, immunotherapy, gene therapy, and the like. Additionally, a person having a greater risk of developing the proliferative disease may receive treatments to inhibit or and/or delay the development of the disease.

Also, provided herein is a liquid pharmaceutical composition comprising the composition comprising the ABOA and the human serum albumin as described herein, and a pharmaceutically acceptable carrier.

In some embodiments, the liquid pharmaceutical composition is a reconstituted solution, reconstituted from the solid composition comprising the ABOA and the human serum albumin as described herein.

In some embodiments, the liquid pharmaceutical composition is an aqueous solution. In some embodiments, the liquid pharmaceutical composition is an aqueous solution substantially free of solvent other than water. In some embodiments, the liquid pharmaceutical composition is an aqueous solution free of solvent other than water.

In some embodiments, the liquid pharmaceutical composition is an aqueous reconstituted solution, reconstituted in a parenterally acceptable aqueous pharmaceutical diluent. In some embodiments, the liquid pharmaceutical composition is an aqueous reconstituted solution, reconstituted in an aqueous infusion fluid.

In some embodiments, the liquid pharmaceutical composition is an injectable pharmaceutical formulation.

In some embodiments, the injectable pharmaceutical formulation is free of solvent other than water. In some embodiments, the injectable pharmaceutical formulation is substantially free of solvent other than water.

In some embodiments, the injectable pharmaceutical formulation is a reconstituted solution, reconstituted from the composition comprising the ABOA and the human serum albumin as described herein. In some embodiments, the injectable pharmaceutical formulation is a reconstituted solution, reconstituted in an aqueous infusion fluid. In some embodiments, the aqueous infusion fluid is normal saline. In some embodiments, the aqueous infusion fluid is a dextrose solution.

Also, provided herein is a composition consisting essentially of ABOA and human serum albumin, wherein the ABOA and the human serum albumin in the composition have a ratio by weight from about 1:1 to about 1:2000.

In some embodiments, the ABOA and the human serum albumin in the composition have a ratio by weight from about 1:5 to about 1:1000, from about 1:10 to about 1:800, from about 1:20 to about 1:600, from about 1:30 to about 1:500, from about 1:30 to about 1:400, from about 1:30 to about 1:300, from about 1:30 to about 1:250, from about 1:30 to about 1:200, from about 1:30 to about 1:150, from about 1:30 to about 1:140, from about 1:30 to about 1:130, from about 1:30 to about 1:120, from about 1:30 to about 1:110, from about 1:30 to about 1:100, from about 1:30 to about 1:90, from about 1:30 to about 1:80, from about 1:30 to about 1:70, from about 1:30 to about 1:60, from about 1:35 to about 1:500, from about 1:35 to about 1:400, from about 1:35 to about 1:300, from about 1:35 to about 1:250, from about 1:35 to about 1:200, from about 1:35 to about 1:150, 1:35 to about 1:140, from about 1:35 to about 1:130, from about 1:35 to about 1:120, from about 1:35 to about 1:110, 1:35 to about 1:100, 1:35 to about 1:90, from about 1:35 to about 1:80, from about 1:35 to about 1:70, from about 1:35 to about 1:60, from about 1:40 to about 1:500, from about 1:40 to about 1:400, from about 1:40 to about 1:300, from about 1:40 to about 1:250, from about 1:40 to about 1:200, from about 1:40 to about 1:150, 1:40 to about 1:140, from about 1:40 to about 1:130, from about 1:40 to about 1:120, from about 1:40 to about 1:110, 1:40 to about 1:100, 1:40 to about 1:90, from about 1:40 to about 1:80, from about 1:40 to about 1:70, or from about 1:40 to about 1:60. In some embodiments, the ABOA and the human serum albumin have a ratio by weight of about 1:20, about 1:30, about 1:35, about 1:40, about 1:45, about 1:50, about 1:55, about 1:60, about 1:65, about 1:70, about 1:75, about 1:80, about 1:90, about 1:100, about 1:110, about 1:120, about 1:130, or about 1:140, about 1:150, about 1:160, about 1:170, about 1:180, about 1:190, about 1:200, about 1:210, about 1:220, about 1:230, about 1:240, about 1:250, or about 1:275, about 1:300, about 1:350, about 1:400, about 1:450, or about 1:500.

In some embodiments, the human serum albumin is a native human serum albumin. In some embodiments, the human serum albumin is a recombinant human serum albumin. In some embodiments, the human serum albumin is a fatty acid free human serum albumin. In some embodiments, the human serum albumin is essentially fatty acid free. In some embodiments, the human serum albumin contains no more than two moles of fatty acids bound to one mole of human serum albumin. In some embodiments, the human serum albumin contains no more than one mole of fatty acids bound to one mole of human serum albumin. In some embodiments, human serum albumin contains no more than 0.5 moles of fatty acids bound to one mole of human serum albumin. In some embodiments, the human serum albumin contains no more than 0.1 moles of fatty acids bound to one mole of human serum albumin. In some embodiments, the human serum albumin contains no more than 0.05 moles of fatty acids bound to one mole of human serum albumin. In some embodiments, the human serum albumin contains no more than 0.01 moles of fatty acids bound to one mole of human serum albumin. In some embodiments, the human serum albumin contains no more than 0.001 moles of fatty acids bound to one mole of human serum albumin. In some embodiments, the human serum albumin contains no more than 0.0005 moles of fatty acids bound to one mole of human serum albumin. In some embodiments, the human serum albumin contains no more than 0.0001 moles of fatty acids bound to one mole of human serum albumin.

In some embodiments, the ABOA can be a pharmaceutically acceptable salt of ABOA. In some embodiments, the ABOA is a hydrochloride salt of ABOA. In some embodiments, ABOA can be in crystal forms, amorphous forms, solvates and hydrates.

In some embodiments, the composition is a clear aqueous solution when the composition is dissolved in an aqueous solution. In some embodiments, the aqueous solution is substantially free of solvent other than water. In some embodiments, the aqueous solution is free of solvent other than water.

In some embodiments, the composition is a clear aqueous solution for at least 1 hour when the composition is dissolved in an aqueous solution. In some embodiments, the composition is a clear aqueous solution for at least 2 hours when the composition is dissolved in an aqueous solution. In some embodiments, the composition is a clear aqueous solution for at least 3 hours when the composition is dissolved in an aqueous solution. In some embodiments, the composition is a clear aqueous solution for at least 4 hours when the composition is dissolved in an aqueous solution. In some embodiments, the composition is a clear aqueous solution for at least 5 hours when the composition is dissolved in an aqueous solution. In some embodiments, the composition is a clear aqueous solution for at least 6 hours when the composition is dissolved in an aqueous solution. In some embodiments, the composition is a clear aqueous solution for at least 8 hours when the composition is dissolved in an aqueous solution. In some embodiments, the composition is a clear aqueous solution for at least 24 hours when the composition is dissolved in an aqueous solution. In some embodiments, the aqueous solution is substantially free of solvent other than water. In some embodiments, the aqueous solution free of solvent other than water.

In some embodiments, the composition is a solid formulation. For example, the solid formulation can be produced in a uniform manner by lyophilization. A skilled artisan would recognize other methods, such as rotary evaporation, that can also produce solid formulations.

In some embodiments, the composition is an aqueous formulation. In some embodiments, the aqueous formulation is substantially free of solvent other than water. In some embodiments, the aqueous formulation is free of solvent other than water.

In some embodiments, the aqueous formulation is a clear aqueous solution. For example, the formulation can be a clear and stable aqueous solution reconstituted from a sterile lyophilized powder. In some embodiments, the aqueous formulation is a clear aqueous solution, wherein the aqueous formulation is substantially free of solvent other than water. In some embodiments, the aqueous formulation is a clear aqueous solution, wherein the aqueous formulation is free of solvent other than water.

In some embodiments, the aqueous formulation has pH value from about 5 to about 8. In some embodiments, the aqueous formulation has pH value from about 5.5 to about 7.8. In some embodiments, the aqueous formulation has pH value from about 6 to about 7.5. In some embodiments, the aqueous formulation has pH value from about 6.5 to about 7.5. In some embodiments, the aqueous formulation has pH value from about 6 to about 6.5. In some embodiments, the aqueous formulation has pH value from about 6.5 to about 7. In some embodiments, the aqueous formulation has pH value from about 7 to about 7.5. In some embodiments, the aqueous formulation has pH value about 6, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5. In some embodiments, the aqueous formulation is substantially free of solvent other than water. In some embodiments, the aqueous formulation is free of solvent other than water.

In some embodiments, the aqueous formulation is a clear aqueous solution, wherein the aqueous formulation has pH value from about 5 to about 8, and wherein the aqueous formulation is substantially free of solvent other than water. In some embodiments, the aqueous formulation is a clear aqueous solution, wherein the aqueous formulation has pH value from about 5 to about 8, and wherein the aqueous formulation is free of solvent other than water.

In some embodiments, the aqueous formulation is a clear aqueous solution for at least 1 hour. In some embodiments, the aqueous formulation is a clear aqueous solution for at least 1 hour at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 2 hours. In some embodiments, the aqueous formulation is a clear aqueous solution for at least 2 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 3 hours. In some embodiments, the aqueous formulation is a clear aqueous solution for at least 3 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 6 hours. In some embodiments, the aqueous formulation is a clear aqueous solution for at least 6 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 24 hours. In some embodiments, the aqueous formulation is a clear aqueous solution for at least 24 hours at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least 3 days. In some embodiments, the aqueous formulation is a clear aqueous solution for at least 3 days when dissolved in an aqueous solution at a temperature from about 1° C. to about 35° C., about 1° C. to about 10° C., about 10° C. to about 20° C., about 20° C. to about 35° C., or about 1° C., about 5° C., about 10° C., about 15° C., about 20° C., about 25° C., about 30° C., or about 35° C. In some embodiments, the aqueous formulation is a clear aqueous solution for at least about 1 hour, 2 hours, 3 hours, 4 hours, 5 hours, 6 hours, 8 hours, or 24 hours. In some embodiments, the aqueous formulation is substantially free of solvent other than water. In some embodiments, the aqueous formulation is free of solvent other than water.

Also, provided herein is a pharmaceutical composition comprising the composition consisting essentially of the ABOA and the human serum albumin as described herein, and a pharmaceutically acceptable carrier.

In some embodiments, the pharmaceutical composition further comprises at least one anti-cancer drug (e.g., any one of the anti-cancer drugs as described herein).

Also, provided herein is a method of treating a proliferative disease comprising the step of administering to a subject in need thereof a pharmaceutical composition comprising the composition consisting essentially of the ABOA and the human serum albumin as described herein, and a pharmaceutically acceptable carrier.

Also, provided herein is a method of treating a cancer (e.g., any one of cancers described herein), the method comprising the step of administering to a subject in need thereof of a therapeutically effective amount of a pharmaceutical composition comprising the composition consisting essentially of the ABOA and the human serum albumin as described herein, and a pharmaceutically acceptable carrier.

In some embodiments, the cancer is any one of cancers described herein.

In some embodiments, the cancer is a solid tumor. In some embodiments, the cancer is a prostate cancer. In some embodiments, the cancer is a metastatic castration-resistant prostate cancer.

The methods described herein may be performed alone or in conjunction with another therapy, such as surgery, radiation, chemotherapy, immunotherapy, gene therapy, and the like. Additionally, a person having a greater risk of developing the proliferative disease may receive treatments to inhibit or and/or delay the development of the disease.

Kits

The present invention also includes pharmaceutical kits useful, for example, in the treatment or prevention of any one of diseases or disorders referred to herein, which include one or more containers containing a pharmaceutical composition comprising a composition of ABOA and the human serum albumin as described herein. Such kits can further include, if desired, one or more of various conventional pharmaceutical kit components, such as, for example, containers with one or more pharmaceutically acceptable carriers (e.g., water. Saline, or 5% dextrose), additional containers, etc., as will be readily apparent to those skilled in the art. Instructions, either as inserts or as labels, indicating quantities of the components to be administered (e.g., dosage amounts as described herein), guidelines for administration, and/or guidelines for mixing the components, can also be included in the kit.

Methods of Making

Also, provided herein are several methods to prepare a composition comprising a non-covalently bound complex comprising the ABOA and the human serum albumin as described herein, a composition comprising the ABOA and the human serum albumin as described herein, or a composition consisting essentially of the ABOA and the human serum albumin as described herein.

In some embodiments, the present disclosure provides a method of preparing a composition comprising a non-covalently bound complex comprising ABOA and human serum albumin, wherein the ABOA and the human serum albumin in the composition have a ratio by weight from about 1:1 to about 1:2000.

In some embodiments, the present disclosure provides a method of preparing a composition comprising ABOA and human serum albumin, wherein the ABOA and the human serum albumin in the composition have a ratio by weight from about 1:1 to about 1:2000.

In some embodiments, the present disclosure provides a method of preparing a composition consisting essentially of ABOA and human serum albumin, wherein the ABOA and the human serum albumin in the composition have a ratio by weight from about 1:1 to about 1:2000.

In some embodiments, the method comprises mixing an organic solution of ABOA in a polar water-miscible organic solvent and a first aqueous solution containing human serum albumin to form a second aqueous solution, wherein the second aqueous solution is a clear aqueous solution.

In some embodiments, the method further comprises removing said polar water-miscible organic solvent and water from the second aqueous solution.

In some embodiments, the method comprises the steps of:
(i) obtaining an organic solution of ABOA in a polar water-miscible organic solvent;
(ii) obtaining a first aqueous solution of human serum albumin; and
(iii) mixing the organic solution of ABOA and the first aqueous solution of human serum albumin to obtain a second aqueous solution comprising the composition comprising ABOA and human serum albumin as described herein.

A non-limiting embodiments of the method are as follows.

Formation of the Organic Solution

In some embodiments, ABOA is dissolved in a polar organic solvent (e.g., an alcohol such as methanol, ethanol, isopropanol, and/or n-butanol; THF; $CH_3CN$; DMF; or mixtures thereof) to form an organic solution.

As used herein, the term "organic solution" refers to a solution wherein at least one solvent is a non-aqueous solvent and the weight % of the non-aqueous solvent in the mixture of solvents is at least 50%, at least 60%, at least 70% or at least 90%. In some embodiments, organic solution is a solution in which does not comprise water as a solvent.

In some embodiments, the terms "organic solvent" and "non-aqueous solvent" are used interchangeably and refer to a liquid comprising is at least 50%, at least 60%, at least 70%, at least 90%, or at least 95% of a solvent other than water. In some embodiments, organic solvent is polar (e.g., polar aprotic solvent such as tetrahydrofuran, ethyl acetate, acetone, dimethylformamide, acetonitrile, dimethyl sulfoxide or nitromethane; or a polar protic solvent such as an alcohol, or an acid such as formic acid or an acetic acid). In some embodiments, the organic solvent is water-miscible (i.e., can be mixed with water in all proportions) or water-immiscible (i.e., significant proportions of organic solvent/water do not form a solution).

In some embodiments, the organic solvent is polar organic solvent that is miscible in water (e.g., tetrahydrofuran, propylene glycol, propanol, methanol, ethanol, dimethyl sulfoxide, dimethylformamide, acetonitrile or acetone). In some embodiments, the polar organic solvent is an alcohol. In some embodiments, the polar organic solvent is ethanol or methanol, or mixtures thereof. In some embodiments, the polar organic solvent can be ethanol. In some embodiments, the polar organic solvent is methanol.

In some embodiments, the amount of polar organic solvent is from about 0.005 mL to about 10 mL per 1 mg of ABOA. In some embodiments, the amount of polar organic solvent is from about 0.01 mL to about 5 mL per 1 mg of ABOA. In some embodiments, the amount of polar organic solvent is from about 0.05 mL to about 2 mL per 1 mg of ABOA. In some embodiments, the amount of polar organic solvent is from about 0.1 mL to about 1.0 mL per 1 mg of ABOA. In some embodiments, the amount of polar organic solvent is from about 0.2 mL to about 2.0 mL per 1 mg of ABOA. In some embodiments, the amount of polar organic solvent is from about 0.25 mL to about 1.7 mL per 1 mg of ABOA. In some embodiments, the amount of polar organic solvent is about 0.05 mL, about 0.1 mL, about 0.2 mL, about 0.25 mL, about 0.3 mL, about 0.35 mL, about 0.4 mL, about 0.45 mL, about 0.5 mL, about 0.6 mL, about 0.65 mL, about 0.7 mL, about 0.8 mL, about 0.85 mL, about 1 mL, about 1.3 mL, about 1.4 mL, about 1.5 mL, about 1.6 mL, about 1.7 mL, about 1.8 mL, about 1.9 mL, about 2.1 mL, about 2.6 mL, or about 3 mL per 1 mg of ABOA. In some embodiments, the polar organic solvent is methanol and the concentration of ABOA in the methanolic solution is from about 0.005 mM to about 10 mM, from about 0.05 mM to about 7 mM, from about 0.1 mM to about 5 mM, or from about 0.5 mM to about 3 mM, from about 0.5 mM to about 2 mM, or from about 0.6 mM to about 2 mM, or from about 1 mM to about 15 mM, from about 1.5 mM to about 10 mM, or from about 1.8 mM to about 9.5 mM. In some embodiments, the polar organic solvent is methanol and the concentration of ABOA in the methanolic solution is about 0.6 mM, about 0.7 mM, about 0.8 mM, about 0.9 mM, about 1 mM, about 1.1 mM, about 1.2 mM, about 1.3 mM, about 1.4 mM, about 1.5 mM, about 1.6 mM, about 1.7 mM, about 1.8 mM, about 1.9 mM, about 2 mM, about 2.5 mM, about 3 mM, about 3.5 mM, about 5 mM, about 5.5 mM, about 6 mM, about 7 mM, about 8 mM, about 8.5 mM, about 9 mM, or about 9.5 mM.

Formation of the First Aqueous Solution

In some embodiments, a defined amount of human serum albumin is dissolved in an amount of aqueous solvent (e.g., any one of aqueous solvents described herein such as water, 0.9% saline or 5% dextrose) to form a first aqueous solution.

In some embodiments, the amount of aqueous solvent (e.g., water) to prepare the first aqueous solution is from about 1 mL to about 10000 L, from about 2 mL to about 1000 L, from about 3 mL to about 100 L, from about 4 mL to about 10 L, from about 5 mL to about 2 L, from about 6 mL to about 1 L.

In some embodiments, the amount of HSA prepare the first aqueous solution is from about 100 mg to about 1000 kg, from about 150 mg to about 1000 kg, from about 200 mg to about 100 kg, from about 300 mg to about 5 kg, from about 200 mg to about 500 g, or from about 200 mg to about 100 g.

In some embodiments, the amount of aqueous solvent in the first aqueous solution is from about 0.005 mL to about 10 mL per 1 mg of human serum albumin. In some embodiments, the amount of aqueous solvent in the first aqueous solution is from about 0.01 mL to about 5 mL per 1 mg of human serum albumin. In some embodiments, the amount of aqueous solvent in the first aqueous solution is from about 0.01 mL to about 1 mL per 1 mg of human serum albumin. In some embodiments, the amount of aqueous solvent in the first aqueous solution is from about 0.01 mL to about 0.5 mL per 1 mg of human serum albumin. In some embodiments, the amount of aqueous solvent in the first aqueous solution is from about 0.01 mL to about 0.1 mL per 1 mg of human serum albumin. In some embodiments, the amount of aqueous solvent in the first aqueous solution is from about 0.01 mL to about 0.05 mL per 1 mg of human serum albumin. In some embodiments, the amount of aqueous solvent in the first aqueous solution is from about 0.01 mL to about 0.025 mL per 1 mg of human serum albumin. In some embodiments, the amount of aqueous solvent in the first aqueous solution is from about 0.013 mL to about 0.022 mL per 1 mg of human serum albumin. In some embodiments, the amount of aqueous solvent in the first aqueous solution is from about 0.015 mL to about 0.04 mL per 1 mg of human serum albumin. In some embodiments, the amount of aqueous solvent in the first aqueous solution is about 0.007 mL, about 0.01 mL, about 0.015 mL, about 0.02 mL, about 0.025 mL, about 0.03 mL, about 0.035 mL, about 0.04 mL, about 0.045 mL, or about 0.05 mL per 1 mg of human serum albumin. In some embodiments, the amount of aqueous solvent in the first aqueous solution is about 0.02 mL per 1 mg of human serum albumin. In some embodiments, the amount of aqueous solvent (e.g., water) to prepare the first aqueous solution is from about or from about 0.005 mL to about 1 mL, from about 0.015 mL to about 0.5 mL, from about 0.015 mL to about 0.2 mL, from about 0.015 mL to about 0.1 mL, or from about 0.015 mL to about 0.05 mL per 1 mg of HSA. In some embodiments, the amount of aqueous solvent (e.g., water) to prepare the first aqueous solution is about 0.01 mL, about 0.011 mL, about 0.012 mL, about 0.013 mL, about 0.015 mL, about 0.017 mL, about 0.018 mL, about 0.019 mL about 0.02 mL, about 0.021 mL, about 0.022 mL, about 0.023 mL, about 0.024 mL, about 0.025 mL, about 0.026 mL, about 0.027 mL, about 0.028 mL, about 0.029 mL or about 0.03 mL per 1 mg of HSA.

In some embodiments, the amount of HSA in the first aqueous solution is from about 10% w/w to about 25% w/w, or from about 13% w/w to about 22% w/w. In some embodiments, the amount of HSA in the first aqueous solution is about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w or about 25% w/w.

In some embodiments, the preparation of the organic solution and the preparation of the first aqueous solution are performed concurrently.

In some embodiments, the preparation of the organic solution and the preparation of the first aqueous solution are performed sequentially. In some embodiments, the preparation of the organic solution is performed before the preparation of the first aqueous solution. In some embodiments, the preparation of the first aqueous solution is performed before the preparation of the organic solution.

In some embodiments, the range of pH in the first aqueous solution is from about 3 to about 9, from about 4 to about 8, from about 5 to about 7, from about 6 to about 7, from about 3 to about 5, from about 3 to about 7, from about 4 to about 6, from about 5 to about 6, or from about 6 to about 6.5. In some embodiments, the pH of the first aqueous solution is about 4, about 5, about 6, about 6.1, about 6.2, about 6.3, about 6.4, about 6.5, about 6.6, about 6.7, about 6.8, about 6.9, about 7, about 7.5, or about 8.

Formation of the Second Aqueous Solution

In some embodiments, the organic solution of ABOA is mixed with the first aqueous solution of human serum albumin to form a second aqueous solution. In some embodiments, the second aqueous solution is a clear aqueous solution.

In some embodiments, the volume ratio of the amount of water to the amount of the polar organic solvent is in a range from about 1:1 to about 1000:1. In some embodiments, the volume ratio of the amount of water to the amount of the polar organic solvent is in a range from about 1.5:1 to about 100:1. In some embodiments, the volume ratio of the amount of water to the amount of the polar organic solvent is in a range from about 1.5:1 to about 20:1. In some embodiments, the volume ratio of the amount of water to the amount of the polar organic solvent is in a range from about 1.5:1 to about 10:1. In some embodiments, the volume ratio of the amount of water to the amount of the polar organic solvent is in a range from about 2:1 to about 10:1. In some embodiments, the volume ratio of the amount of water to the amount of the polar organic solvent is in a range from about 2:1 to about 3:1. In some embodiments, the volume ratio of the amount of water to the amount of the polar organic solvent is about 1.5:1, about 2:1, about 2.1:1, about 2.2:1, about 2.3:1, about 2.4:1, about 2.5:1, about 3:1, about 4:1, about 5:1, about 6:1, about 7:1, about 8:1, about 9:1, or about 10:1.

In some embodiments, the organic solution is added to the first aqueous solution to form a second aqueous solution. In some embodiments, the organic solution is added dropwise to the first aqueous solution to form a second aqueous solution. In some embodiments, the first aqueous solution is added to the organic solution to form a second aqueous solution. In some embodiments, the mixing is performed with agitation. In some embodiments, the mixing is performed with stirring. In some embodiments, the mixing is performed with shaking.

In some embodiments, the addition is done at the temperature from about 0° C. to about 35° C. In some embodiments, the addition is done at the temperature from about 0° C. to about 25° C. In some embodiments, the addition is done at the temperature from about 0° C. to about 10° C. In some embodiments, the addition is done at the temperature from about 0° C. to about 5° C. In some embodiments, the addition is done at the temperature about 0° C. In some embodiments, the addition is done at the temperature about 5° C. In some embodiments, the addition is done at the temperature about 10° C.

In some embodiments, the time of addition is in a range from about 0.1 min to about 24 hours. In some embodiments, the time of addition is in a range from about 1 min to about 2 hours. In some embodiments, the time of addition is in a range from about 1 min to about 1 hour. In some embodiments, the time of addition is in a range from about 5 min to about 30 min.

In some embodiments, the rate of addition of organic solution to the first aqueous solution is from about 0.01 mL/min to about 100 mL/min, from about 0.02 mL/min to about 50 mL/min, from about 0.05 mL/min to about 20 mL/min, from about 1 mL/min to about 10 mL/min, or from about 0.01 mL/min to about 10 mL/min, from about 0.01 mL/min to about 5 mL/min, from about 0.01 mL/min to about 2 mL/min, from about 0.01 mL/min to about 1 mL/min, from about 0.01 mL/min to about 0.5 mL/min, or from about 0.01 mL/min to about 0.1 mL/min.

In some embodiments, the rate of addition of organic solution to the first aqueous solution is about 0.01 mL/min, 0.02 mL/min, 0.03 mL/min, 0.04 mL/min, 0.05 mL/min, 0.1 mL/min, 0.2 mL/min, 0.3 mL/min, 0.5 mL/min, 0.6 mL/min, 0.8 mL/min, 1 mL/min, 1.5 mL/min, 2 mL/min, 3 mL/min, 5 mL/min or 10 mL/min In some embodiments, the resulting composition comprising the ABOA and the human serum albumin can have any ratio by weight of the ABOA to the human serum albumin as described herein. In some embodiments, the human serum albumin is a fatty acid free human serum albumin. In some embodiments, the human serum albumin is essentially fatty acid free.

In some embodiments, the range of pH in the second aqueous solution is from about 3 to about 9, from about 4 to about 8, from about 5 to about 7, from about 6 to about 7, from about 3 to about 5, from about 3 to about 7, from about 4 to about 6, from about 5 to about 6, or from about 6 to about 6.5. In some embodiments, the pH of the second aqueous solution is about 4, about 5, about 6, about 6.1, about 6.2, about 6.3, about 6.4, about 6.5, about 6.6, about 6.7, about 6.8, about 6.9, about 7, about 7.5, or about 8.

Removal of Organic Solvent

In some embodiments, upon completion of mixing of the organic solution with the first aqueous solution to form the second aqueous solution, the polar organic solvent is removed from the second aqueous solution.

In some embodiments, the polar organic solvent is removed under reduced pressure. In some embodiments, the polar organic solvent is removed using rotary evaporation. In some embodiments, the polar organic solvent is removed under a vacuum.

In some embodiments, the removal of the polar organic solvent yields a clear aqueous solution. In some embodiments, water is removed from the aqueous under a vacuum. In some embodiments, water is removed from the aqueous solution using rotary evaporation. In some embodiments, water is removed from the aqueous solution by lyophilization.

In some embodiments, the solvents including both water and organic solvent are removed from the second aqueous solution simultaneously to provide a solid composition. In some embodiments, the solvents are removed under a vacuum. In some embodiments, the solvents are removed using rotary evaporation. In some embodiments, the solvents are removed by lyophilization. In some embodiments, the second aqueous solution was filtered before removal of the solvents.

Removal of Water from the Second Aqueous Solution

In some embodiments, upon removal of the organic solvent from the second aqueous solution, the water can be removed from the second aqueous solution to provide a solid composition.

In some embodiments, the second aqueous solution is filtered before removal of water. For example, the second aqueous solution can be filtered by a 0.22 micron filter before removal of water.

As used herein, the term "micron" refers to a unit of measure of one one-thousandth of a millimeter.

In some embodiments, the water is removed under a vacuum. In some embodiments, the water is removed using rotary evaporation. In some embodiments, the water is removed by lyophilization.

Reconstitution of the Solid

In some embodiments the solid comprising the ABOA and the human serum albumin is mixed with an aqueous solution. In some embodiments, the aqueous solution is a saline solution. In some embodiments, the aqueous solution is a 5% Dextrose water solution. In some embodiments, the mixing is the addition of the aqueous solution to the solid. In some embodiments, the mixing is the addition of the solid to the aqueous solution. In some embodiments, the mixing reconstitutes the solid. In some embodiments, the mixing yields a clear aqueous solution.

Unless otherwise defined, all technical and scientific terms used herein have the same meaning as commonly understood by one of ordinary skill in the art to which this disclosure belongs. Methods and materials are described herein for use in the present disclosure; other suitable methods and materials known in the art can also be used. The materials, methods, and examples are illustrative only and not intended to be limiting. All publications, patent applications, patents, and other references mentioned herein are incorporated by reference in their entirety. In case of conflict, the present specification, including definitions, will control.

Composition Prepared by the Process

In some embodiments, the present disclosure provides a composition comprising ABOA and human serum albumin, wherein the ABOA and the human serum albumin in the composition have a ratio by weight as described herein (e.g., from about 1:1 to about 1:2000), produced by a method comprising the steps of:

(i) obtaining an organic solution of ABOA in a polar water-miscible organic solvent;

(ii) obtaining a first aqueous solution of human serum albumin; and (iii) mixing the organic solution of ABOA and the first aqueous solution of human serum albumin to obtain a second aqueous solution comprising the composition comprising ABOA and human serum albumin.

In some embodiments, the ABOA and the human serum albumin in the composition have a ratio by weight from about 1:5 to about 1:1000, from about 1:10 to about 1:800, from about 1:20 to about 1:600, from about 1:30 to about 1:500, from about 1:30 to about 1:400, from about 1:30 to about 1:300, from about 1:30 to about 1:250, from about 1:30 to about 1:200, from about 1:30 to about 1:150, about 1:30 to about 1:140, from about 1:30 to about 1:130, from about 1:30 to about 1:120, from about 1:30 to about 1:110, about 1:30 to about 1:100, about 1:30 to about 1:90, from about 1:30 to about 1:80, from about 1:30 to about 1:70, from about 1:30 to about 1:60, from about 1:35 to about 1:500, from about 1:35 to about 1:400, from about 1:35 to about 1:300, from about 1:35 to about 1:250, from about 1:35 to about 1:200, from about 1:35 to about 1:150, 1:35 to about 1:140, from about 1:35 to about 1:130, from about 1:35 to about 1:120, from about 1:35 to about 1:110, 1:35 to about 1:100, 1:35 to about 1:90, from about 1:35 to about 1:80, from about 1:35 to about 1:70, from about 1:35 to about 1:60, from about 1:40 to about 1:500, from about 1:40 to about 1:400, from about 1:40 to about 1:300, from about 1:40 to about 1:250, from about 1:40 to about 1:200, from about 1:40 to about 1:150, 1:40 to about 1:140, from about 1:40 to about 1:130, from about 1:40 to about 1:120, from about 1:40 to about 1:110, 1:40 to about 1:100, 1:40 to about 1:90, from about 1:40 to about 1:80, from about 1:40 to about 1:70, or from about 1:40 to about 1:60. In some embodiments, the ABOA and the human serum albumin have a ratio by weight of about 1:20, about 1:30, about 1:35, about 1:40, about 1:45, about 1:50, about 1:55, about 1:60, about 1:65, about 1:70, about 1:75, about 1:80, about 1:90, about 1:100, about 1:110, about 1:120, about 1:130, or about 1:140, about 1:150, about 1:160, about 1:170, about 1:180, about 1:190, about 1:200, about 1:210, about 1:220, about 1:230, about 1:240, about 1:250, or about 1:275, about 1:300, about 1:350, about 1:400, about 1:450, or about 1:500.

In some embodiments, the ABOA can be a pharmaceutically acceptable salt of ABOA. In some embodiments, ABOA can be in crystal forms, amorphous forms, solvates and hydrates.

In some embodiments, the human serum albumin is essentially fatty acid free.

In some embodiments, the composition comprises a non-covalently bound complex comprising ABOA and human serum albumin.

In some embodiments, the range of pH in the first aqueous solution is from about 3 to about 9, from about 4 to about 8, from about 5 to about 7, from about 6 to about 7, from about 3 to about 5, from about 3 to about 7, from about 4 to about 6, from about 5 to about 6, or from about 6 to about 6.5. In some embodiments, the pH of the first aqueous solution is about 4, about 5, about 6, about 6.1, about 6.2, about 6.3, about 6.4, about 6.5, about 6.6, about 6.7, about 6.8, about 6.9, about 7, about 7.5, or about 8.

In some embodiments, the polar water-miscible organic solvent is an alcohol selected from the group consisting of methanol, ethanol, isopropanol, n-butanol, and mixtures thereof.

In some embodiments, the polar water-miscible organic solvent is selected from methanol, ethanol, and mixtures thereof.

In some embodiments, the polar water-miscible organic solvent is methanol.

In some embodiments, the aqueous solvent is water, 0.9% saline or 5% dextrose.

In some embodiments, the polar water-miscible organic solvent is methanol and the aqueous solvent in the first aqueous solution is water.

In some embodiments, the polar water-miscible organic solvent is methanol and the aqueous solvent in the first aqueous solution is 0.9% saline In some embodiments, the polar water-miscible organic solvent is methanol and the aqueous solvent in the first aqueous solution is 5% dextrose.

In some embodiments, the mixing comprises adding the organic solution to the first aqueous solution. In some embodiments, wherein the mixing comprises adding the first aqueous solution to the organic solution. In some embodiments, the adding is carried out dropwise. In some embodiments, the adding is carried out for a period of time from several minutes to several hours. In some embodiments, the adding is carried out for a period of time from 2 min to 24 hours. In some embodiments, the adding is carried out for a period of time from 2 min minutes to 12 hours, from 2 min to 6 hours, from 3 min to 3 hours, from 2 min to 1 hour, from 2 min to 30 min, or from 2 min to 25 min.

In some embodiments, the mixing is carried out at a temperature from about 0° C. to about 25° C. In some embodiments, mixing is carried out at ambient temperature (e.g., about 25° C.). In some embodiments, the mixing is carried out at a temperature from about 0° C. to about 5° C. In some embodiments, the mixing is carried out at about 0° C.

In some embodiments, the volume ratio of the amount of aqueous solvent to the amount of the organic solvent in the second aqueous solution is in a range from about 1:1 to about 1000:1. In some embodiments, the volume ratio of the amount of aqueous solvent to the amount of the organic solvent in the second aqueous solution is in a range from about 1.5:1 to about 100:1. In some embodiments, the volume ratio of the amount of aqueous solvent to the amount of the organic solvent in the second aqueous solution is in a range from about 1.5:1 to about 20:1. In some embodiments, the volume ratio of the amount of aqueous solvent to the amount of the organic solvent in the second aqueous solution is in a range from about 1.5:1 to about 10:1. In some embodiments, the volume ratio of the amount of aqueous solvent to the amount of the organic solvent in the second aqueous solution is in a range from about 2:1 to about 10:1. In some embodiments, the volume ratio of the amount of aqueous solvent to the amount of the organic solvent in the second aqueous solution is about 1.5:1, about 2:1, about 2.1:1, about 2.2:1, about 2.3:1, about 2.4:1, about 2.5:1, about 3:1, about 4:1, about 5:1, about 6:1, about 7:1, about 8:1, about 9:1, or about 10:1. In some embodiments, the aqueous solvent is water. In some embodiments, the aqueous solvent is water and the organic solvent is an alcohol. In some embodiments, the aqueous solvent is water and the organic solvent is methanol.

In some embodiments, the volume ratio of the amount of water to the amount of the polar organic solvent is in a range from about 2:1 to about 3:1.

In some embodiments, the volume ratio of the amount of water to the amount of the polar organic solvent is in a range from about 2:1 to about 2.5:1.

In some embodiments, the composition is prepared by further comprising the step of removing the polar water-miscible organic solvent from the second aqueous solution to obtain a third aqueous solution comprising the composition comprising ABOA and human serum albumin. In some embodiments, the composition is prepared by further comprising the step of removing aqueous solvent from the third aqueous solution to obtain the composition comprising ABOA and human serum albumin.

In some embodiments, the composition is prepared by further comprising the step of removing the organic solvent (e.g. methanol) and the aqueous solvent (e.g., water) from the second aqueous solution to obtain the composition comprising ABOA and human serum albumin.

In some embodiments, the removing as carried out in vacuum (e.g., using the rotovap). In some embodiments, the removing is carried out by lyophilization.

In some embodiments, the composition forms a clear aqueous solution when the composition is dissolved in an aqueous solvent, and wherein the solubility of the composition in the aqueous solution is at least 10 mg/ml.

In some embodiments, the composition is a solid formulation

In some embodiments, the composition is an aqueous formulation. In some embodiments, the aqueous formulation is substantially free of solvent other than water. In some embodiments, the aqueous formulation is free of a surfactant. In some embodiments, the surfactant is selected from the group consisting of CREMOPHOR® surfactants and Polysorbate 80.

In some embodiments, the aqueous formulation is a clear aqueous solution. In some embodiments, the aqueous formulation is a clear aqueous solution for at least 1 hour, at least 2 hours, at least 3 hours, at least 4 hours, at least 5 hours, at least 6 hours, at least 8 hours, or at least 24 hours.

In some embodiments, the present disclosure provides a pharmaceutical composition comprising the composition as prepared by a process as described herein, and a pharmaceutically acceptable carrier.

In some embodiments, the present disclosure provides a method of treating a cancer, the method comprising the step of administering to a subject in need thereof a therapeutically effective amount of the pharmaceutical composition as described herein.

In some embodiments, the cancer is a solid tumor. In some embodiments, the cancer is a prostate cancer. In some embodiments, the cancer is a metastatic castration-resistant prostate cancer.

EXAMPLES

Materials and Methods

HPLC analysis: The HPLC system used herein is a SHIMADZU LC-10AT vp series system, which consists of a SHIMADZU LC-10AT vp pump, a manual injector, a SHIMADZU CTO-10AS vp column oven, a SHIMADZU SPD-10A vp wavelength detector, and a SHIMADZU LC solution workstation. Waters XTERRA RP10 column (4.6 mm×150 mm, 5 μm) is used as an analytical HPLC column. The column oven temperature is 30° C. Mobile phase is composed of methanol and water (70:30, v/v) and pumped at a flow rate of 1 ml/minute. The effluent is detected at a wavelength of 254 nm using a UV detector. The sample injection amount is 20 μl.

Example 1: Synthesis of ABOA

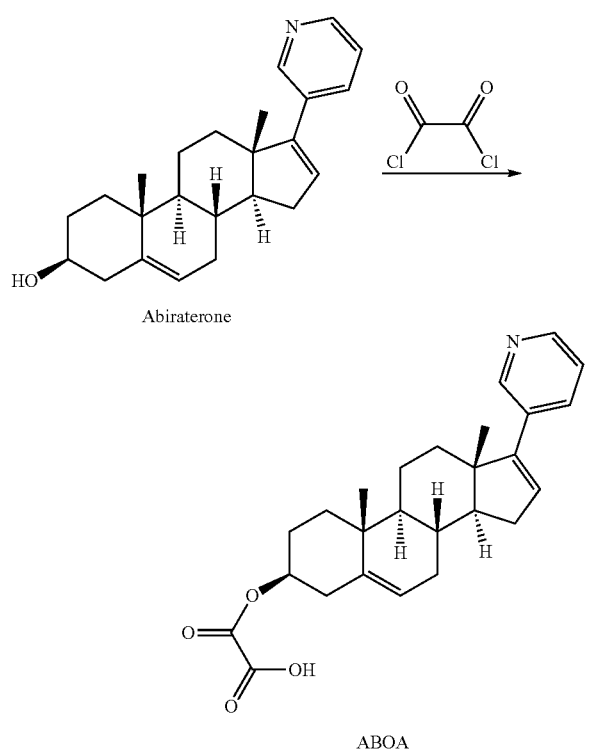

To a solution of Oxalyl chloride (1.1 g, 8.7 mmol) in dichloromethane (25 mL) was added Abiraterone (1 g, 2.9 mmol) portionwise at 0° C. After the addition, the mixture was stirred at 0° C. for an additional 30 minutes. Then $H_2O$ (50 mL) was slowly added into the reaction mixture. The resulting precipitated white solid was filtered and washed with $Et_2O$ to give ABOA (1.1 g).

$^1$H NMR (300 MHz, DMSO-d6) δ: 1.0-1.2 (d, 8H), 1.5 (m, 1H), 1.6-1.8 (m, 6H), 1.9 (d, 2H), 2.0-2.3 (m, 3H), 2.4-2.5 (m, 1H), 2.5-2.6 (d, 2H), 4.7-4.8 (d, 2H), 5.5 (s, 1H), 6.5-6.6 (s, 1H), 7.9-8.0 (t, 1H), 8.5 (d, 1H), 8.7-8.8 (d, 1H), 8.9 (s, 1H).

LC-MS: m/z=422.5 $(M+1)^+$.

Example 2: Composition Comprising ABOA and Human Serum Albumin (HSA)

The ratio by weight of ABOA to HSA prepared was about 1:50.

ABOA (5 mg) was dissolved in methanol (2.1 ml) in a vial to give a clear solution. HSA (250 mg) (native fatty acid free human serum albumin purchased from SeraCare Life Sciences, product code: HS-455-80, which contains fatty acids <0.2 mg/gm) as a powder was dissolved in 5 ml of water in a round bottom flask. The methanol solution of ABOA was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution. This aqueous solution stays clear with no precipitation after 1 hour, 2 hours, 3 hours, and 4 hours at room temperature.

Example 3: Composition Comprising ABOA and Human Serum Albumin (HSA)

The ratio by weight of ABOA to HSA prepared was about 1:45.

ABOA (5 mg) was dissolved in methanol (1.7 ml) in a vial to give a clear solution. HSA (225 mg) (native fatty acid free human serum albumin purchased from SeraCare Life Sciences, product code: HS-455-80, which contains fatty acids <0.2 mg/gm) as a powder was dissolved in 4 ml of water in a round bottom flask. The methanol solution of ABOA was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution. This aqueous solution stays clear with no precipitation after 1 hour, 2 hours, 3 hours, 4 hours, and 5 hours at room temperature.

Example 4: Composition Comprising ABOA and Human Serum Albumin (HSA)

The ratio by weight of ABOA to HSA prepared was about 1:40.

ABOA (5 mg) was dissolved in methanol (1.7 ml) in a vial to give a clear solution. HSA (200 mg) (native fatty acid free human serum albumin purchased from SeraCare Life Sciences, product code: HS-455-80, which contains fatty acids <0.2 mg/gm) as a powder was dissolved in 4 ml of water in a round bottom flask. The methanol solution of ABOA was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution. This aqueous solution stays clear with no precipitation after 1 hour, 2 hours, 3 hours, 4 hours, and 5 hours at room temperature.

Example 5: Composition Comprising ABOA and Human Serum Albumin (HSA)

The ratio by weight of ABOA to HSA prepared was about 1:75.

ABOA (4 mg) was dissolved in methanol (2.6 ml) in a vial to give a clear solution. HSA (300 mg) (native fatty acid free human serum albumin purchased from SeraCare Life Sciences, product code: HS-455-80, which contains fatty acids <0.2 mg/gm) as a powder was dissolved in 6 ml of water in a round bottom flask. The methanol solution of ABOA was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution.

Example 6: Composition Comprising ABOA and Human Serum Albumin (HSA)

The ratio by weight of ABOA to HSA prepared was about 1:150.

ABOA (2 mg) was dissolved in methanol (2.6 ml) in a vial to give a clear solution. HSA (300 mg) (native fatty acid free human serum albumin purchased from SeraCare Life Sciences, product code: HS-455-80, which contains fatty acids <0.2 mg/gm) as a powder was dissolved in 6 ml of water in a round bottom flask. The methanol solution of ABOA was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution.

Example 7: Composition Comprising ABOA and Human Serum Albumin (HSA)

The ratio by weight of ABOA to HSA prepared was about 1:200.

ABOA (2 mg) was dissolved in methanol (3.4 ml) in a vial to give a clear solution. HSA (400 mg) (native fatty acid free human serum albumin purchased from SeraCare Life Sciences, product code: HS-455-80, which contains fatty acids <0.2 mg/gm) as a powder was dissolved in 8 ml of water in a round bottom flask. The methanol solution of ABOA was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution.

Example 8: Composition Comprising ABOA and Human Serum Albumin (HSA)

The ratio by weight of ABOA to HSA prepared was about 1:35.

ABOA (5 mg) was dissolved in methanol (1.3 ml) in a vial to give a clear solution. HSA (175 mg) (native fatty acid free human serum albumin purchased from SeraCare Life Sciences, product code: HS-455-80, which contains fatty acids <0.2 mg/gm) as a powder was dissolved in 3 ml of water in a round bottom flask. The methanol solution of ABOA was added slowly dropwise into the flask of the HSA solution with rapid stirring at 0° C. Upon completion of the addition, a clear solution was obtained. Then, the methanol in the solution was removed under vacuum to give a slightly cloudy solution. The resulting aqueous solution was lyophilized overnight to give a white solid.

A sample of 100 mg of the lyophilized solid was reconstituted by adding 2 mL water to give a slightly cloudy solution. This aqueous solution stays slightly cloudy with no precipitation after 5 hours at room temperature.

Example 9: Composition Comprising ABOA and Human Serum Albumin (HSA)

The ratio by weight of ABOA to HSA prepared was about 1:30.

ABOA (5 mg) was dissolved in methanol (1.3 ml) in a vial to give a clear solution. HSA (150 mg) (native fatty acid free human serum albumin purchased from SeraCare Life Sciences, product code: HS-455-80, which contains fatty acids <0.2 mg/gm) as a powder was dissolved in 3 ml of water in a round bottom flask. The methanol solution of ABOA was added slowly dropwise into the flask of the HSA solution with rapid stirring at 0° C. Upon completion of the addition, a clear solution was obtained. Then, the methanol in the solution was removed under vacuum to give a slightly cloudy solution. The resulting aqueous solution was lyophilized overnight to give a white solid.

A sample of 100 mg of the lyophilized solid was reconstituted by adding 2 mL water to give a slightly cloudy solution. White precipitation was formed in the solution after 2 hours at room temperature.

Example 10: Composition Comprising ABOA and Human Serum Albumin (HSA)

The ratio by weight of ABOA to HSA prepared was about 1:150.

ABOA (2 mg) was dissolved in methanol (2.6 ml) in a vial to give a clear solution. A solution of HSA (300 mg, 1.5 ml) (20% human serum albumin solution for infusion (product name: AlbuRx) from CSL Behring) was added into 4.5 ml of water to give a HSA solution (6 ml) in a round bottom flask. The methanol solution of ABOA was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution.

Example 11: Composition Comprising ABOA and Human Serum Albumin (HSA)

The ratio by weight of ABOA to HSA prepared was about 1:100.

ABOA (4 mg) was dissolved in methanol (3.4 ml) in a vial to give a clear solution. A solution of HSA (400 mg, 2 ml) (20% human serum albumin solution for infusion (product name: AlbuRx) from CSL Behring) was added into 6 ml of water to give a HSA solution (8 ml) in a round bottom flask. The methanol solution of ABOA was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution. This aqueous solution stays clear with no precipitation after 1 hour, 2 hours, 3 hours, and 24 hours at room temperature.

Example 12: Composition Comprising ABOA and Human Serum Albumin (HSA)

The ratio by weight of ABOA to HSA prepared was about 1:75.

ABOA (4 mg) was dissolved in methanol (2.6 ml) in a vial to give a clear solution. A solution of HSA (300 mg, 1.5 ml) (20% human serum albumin solution for infusion (product name: AlbuRx) from CSL Behring) was added into 4.5 ml of water to give a HSA solution (6 ml) in a round bottom flask. The methanol solution of ABOA was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution. This aqueous solution stays clear with no precipitation after 1 hour, 2 hours, 3 hours, and 24 hours at room temperature.

Example 13: Composition Comprising ABOA and Human Serum Albumin (HSA)

The ratio by weight of ABOA to HSA prepared was about 1:50.

ABOA (4 mg) was dissolved in methanol (1.7 ml) in a vial to give a clear solution. A solution of HSA (200 mg, 1 ml) (20% human serum albumin solution for infusion (product name: AlbuRx) from CSL Behring) was added into 3 ml of water to give a HSA solution (4 ml) in a round bottom flask. The methanol solution of ABOA was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution. This aqueous solution stays clear with no precipitation after 1 hour, 2 hours, 3 hours, and 24 hours at room temperature.

Example 14: Composition Comprising ABOA and Human Serum Albumin (HSA)

The ratio by weight of ABOA to HSA prepared was about 1:45.

ABOA (4 mg) was dissolved in methanol (1.7 ml) in a vial to give a clear solution. A solution of HSA (180 mg, 0.9 ml) (20% human serum albumin solution for infusion (product name: AlbuRx) from CSL Behring) was added into 3 ml of water to give a HSA solution (3.9 ml) in a round bottom flask. The methanol solution of ABOA was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution. This aqueous solution stays clear with no precipitation after 1 hour, 2 hours, 3 hours, and 24 hours at room temperature.

Example 15: Composition Comprising ABOA and Human Serum Albumin (Recombinant Human Serum Albumin)

The ratio by weight of ABOA to HSA prepared was about 1:75.

ABOA (3 mg) was dissolved in methanol (2.1 ml) in a vial to give a clear solution. HSA (225 mg) (fatty acid free recombinant human serum albumin (no fatty acids detected) purchased from Wuhan Healthgen Biotechnology Corp., www.oryzogen.com) as a powder was dissolved in 5 ml of water in a round bottom flask. The methanol solution of ABOA was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution.

Example 16: Composition Comprising ABOA and Human Serum Albumin (HSA)

The ratio by weight of ABOA to HSA prepared was about 1:40.

ABOA (4 mg) was dissolved in methanol (1.4 ml) in a vial to give a clear solution. A solution of HSA (160 mg, 0.8 ml) (20% human serum albumin solution for infusion (product name: AlbuRx) from CSL Behring) was added into 2.4 ml of water to give a HSA solution (3.2 ml) in a round bottom flask. The methanol solution of ABOA was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a clear solution. This aqueous solution stays clear with no precipitation after 1 hour, 2 hours, 3 hours, 4 hours, 5 hours, 6 hours, 7 hours, 8 hours, and 24 hours at room temperature.

Example 17: Composition Comprising ABOA and Human Serum Albumin (HSA)

The ratio by weight of ABOA to HSA prepared was about 1:35.

ABOA (4 mg) was dissolved in methanol (1.2 ml) in a vial to give a clear solution. A solution of HSA (140 mg, 0.7 ml) (20% human serum albumin solution for infusion (product name: AlbuRx) from CSL Behring) was added into 2.1 ml of water to give a HSA solution (2.8 ml) in a round bottom flask. The methanol solution of ABOA was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a slightly cloudy solution. This aqueous solution stays slightly cloudy with no precipitation after 1 hour, 4 hours, and 6 hours at room temperature.

Example 18: Composition Comprising ABOA and Human Serum Albumin (HSA)

The ratio by weight of ABOA to HSA prepared was about 1:30.

ABOA (4 mg) was dissolved in methanol (1.0 ml) in a vial to give a clear solution. A solution of HSA (120 mg, 0.6 ml) (20% human serum albumin solution for infusion (product name: AlbuRx) from CSL Behring) was added into 1.8 ml of water to give a HSA solution (2.4 ml) in a round bottom flask. The methanol solution of ABOA was added slowly dropwise into the flask of the HSA solution with rapid stirring at 0° C. Upon completion of the addition, a clear solution was obtained. Then, the methanol in the solution was removed under vacuum to give a clear solution. The resulting clear aqueous solution was lyophilized overnight to give a white solid.

A sample of 100 mg of the lyophilized solid was reconstituted by adding 2 mL water to give a slightly cloudy solution. This aqueous solution stays slightly cloudy with some white precipitations after 1 hour at room temperature.

Example 19: Composition Comprising ABOA and Human Serum Albumin (HSA)

The ratio by weight of ABOA to HSA prepared was about 1:50.

ABOA (50 mg) was dissolved in methanol (14.1 ml) in a vial to give a clear solution. HSA (2500 mg) (native fatty acid free human serum albumin purchased from SeraCare Life Sciences, product code: HS-455-80, which contains fatty acids <0.2 mg/gm) as a powder was dissolved in 33 ml of water in a round bottom flask. The methanol solution of ABOA was added slowly dropwise into the flask of the HSA solution with rapid stirring at 0° C. Upon completion of the addition, a clear solution was obtained. Then, the methanol in the solution was removed under vacuum to give a clear solution. The clear aqueous solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution. This aqueous solution stays clear with no precipitation after 1 hour, 2 hours, 3 hours, and 4 hours at room temperature.

Example 20: Composition Comprising ABOA and Human Serum Albumin (HSA)

The ratio by weight of ABOA to HSA prepared was about 1:45.

ABOA (80 mg) was dissolved in methanol (20.6 ml) in a vial to give a clear solution. HSA (3600 mg) (native fatty acid free human serum albumin purchased from SeraCare Life Sciences, product code: HS-455-80, which contains fatty acids <0.2 mg/gm) as a powder was dissolved in 48 ml of water in a round bottom flask. The methanol solution of ABOA was added slowly dropwise into the flask of the HSA solution with rapid stirring at 0° C. Upon completion of the addition, a clear solution was obtained. Then, the methanol in the solution was removed under vacuum to give a clear solution. The clear aqueous solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution.

Example 21: Measuring pH Value of the Clear Aqueous Solution of Composition Comprising ABOA and Human Serum Albumin (HSA)

500 mg of the lyophilized solid comprising the composition comprising ABOA and HSA (the ratio by weight about 1:50) from Example 19 was dissolved in 10 ml of water to give a clear aqueous solution. The clear aqueous solution was kept at about 25° C. and measured for pH value. The pH value of the clear aqueous solution is 6.24 (3 measurements: 6.24, 6.25, and 6.23).

250 mg of the lyophilized solid comprising the composition comprising ABOA and HSA (the ratio by weight about 1:50) from Example 19 was dissolved in 10 ml of water to give a clear aqueous solution. The clear aqueous solution was kept at about 25° C. and measured for pH value. The pH value of the clear aqueous solution is 6.26 (3 measurements: 6.25, 6.26, and 6.26).

250 mg of the lyophilized solid comprising the composition comprising ABOA and HSA (the ratio by weight about 1:50) from Example 19 was dissolved in 10 ml of 0.9% saline, which had pH value about 5.41, to give a clear aqueous solution. The clear aqueous solution was kept at about 25° C. and measured for pH value. The pH value of the clear aqueous solution is 6.20 (3 measurements: 6.20, 6.20, and 6.19).

250 mg of the lyophilized solid comprising the composition comprising ABOA and HSA (the ratio by weight about 1:50) from Example 19 was dissolved in 10 ml of 5% Dextrose solution, which had pH value about 4.40, to give a clear aqueous solution. The clear aqueous solution was kept at about 25° C. and measured for pH value. The pH value of the clear aqueous solution is 6.19 (3 measurements: 6.19, 6.20, and 6.19).

Example 22: Measuring the Correlation Between HPLC Peak Area and the ABOA Concentration Methanol solutions of ABOA in 7 different concentrations, 0.05 mg/ml, 0.1 mg/ml, 0.15 mg/ml, 0.2 mg/ml, 0.3 mg/ml, 0.4 mg/ml and 0.5 mg/ml, were prepared. The 7

ABOA methanol solutions were analyzed in HPLC. The peak area and concentration of ABOA were correlated using linear regression. The linear regression data is shown as below.

Y (peak area)=23621+1.80451E7*X (concentration), R=0.99992, P<0.0001.

Example 23: Measuring the ABOA Concentrations in the Aqueous Solutions Before and after the Filtration at 0 Hour, and after the Filtration at 1 Hour, 2 Hours, 3 Hours, 4 Hours, 5 Hours, and 6 Hours 2.1 g of the lyophilized solid of the composition comprising ABOA and HSA (the ratio by weight about 1:45) from Example 20 was dissolved in 42 ml of water to give a clear aqueous solution, which was kept at about 25° C. Immediately after the lyophilized solid was dissolved in water, 6 ml of the clear aqueous solution was taken out from the 42 ml solution. Then 1 ml of the solution was taken out from the 6 ml clear aqueous solution to give the solution ABOA-0-0h, and the remaining 5 ml of the solution was filtered by the same 0.22 micron aqueous phase filter at 1 ml at a time to give the solutions ABOA-1-0h, ABOA-2-0h, ABOA-3-0h, ABOA-4-0h, and ABOA-5-0h. To 200 μl of the solutions ABOA-0-0h and ABOA-5-0h were added 800 μl of acetonitrile separately. The mixtures were vortexed for seconds and then centrifuged at 4,000 g for 5 minutes. The supernatants were removed and collected followed by injection on HPLC. The same procedure was repeated 2 more times for each of solutions ABOA-0-0h and ABOA-5-0h. Based on the HPLC data and the measurement data of example 22, the ABOA concentrations of the solutions of ABOA-0-0h, and ABOA-5-0h have been calculated and shown in the Table 1. At 0 hour, the ABOA concentration of the clear aqueous solution after the filtration was about 100% of the ABOA concentration of the clear aqueous solution before the filtration.

TABLE 1

| Solution Number | ABOA Concentration (mg/ml) | Average ABOA Concentration (mg/ml) |
| --- | --- | --- |
| ABOA-0-0h-1 | 1.006 | 1.006 |
| ABOA-0-0h-2 | 1.006 | |
| ABOA-0-0h-3 | 1.006 | |
| ABOA-5-0h-1 | 1.007 | 1.006 |
| ABOA-5-0h-2 | 1.003 | |
| ABOA-5-0h-3 | 1.007 | |

At 1 hour, 5 ml of the clear aqueous solution was taken out from the remaining 36 ml of the aqueous solution. Then 1 ml of the solution was taken out from the 5 ml clear aqueous solution and filtered by a 0.22 micron aqueous phase filter to give the solution ABOA-1-1h, and the remaining 4 ml of the solution was filtered by the same 0.22 micron aqueous phase filter at 1 ml at a time to give the solutions ABOA-2-1h, ABOA-3-1h, ABOA-4-1h, and ABOA-5-1h. To 200 μl of the solution ABOA-5-1h was added 800 μl of acetonitrile. The mixture was vortexed for seconds and then centrifuged at 4,000 g for 5 minutes. The supernatant was removed and collected followed by injection on HPLC. The same procedure was repeated 2 more times for the solution ABOA-5-1h. Based on the HPLC data and the measurement data of example 22, the ABOA concentrations of the solution ABOA-5-1h have been calculated and shown in the Table 2.

At 1 hour, the ABOA concentration of the clear aqueous solution after the filtration was about 98.72% of the ABOA concentration of the clear aqueous solution at 0 hour before the filtration.

TABLE 2

| Solution Number | ABOA Concentration (mg/ml) | Average ABOA Concentration (mg/ml) |
| --- | --- | --- |
| ABOA-5-1h-1 | 0.9923 | 0.9931 |
| ABOA-5-1h-2 | 0.9947 | |
| ABOA-5-1h-3 | 0.9922 | |

At 2 hours, 5 ml of the clear aqueous solution was taken out from the remaining 31 ml of the aqueous solution. The experiments were done for the 5 ml of the clear aqueous solution taken out at 2 hour using the same protocol as for the 5 ml of the clear aqueous solution taken out at 1 hour. Based on the HPLC data and the measurement data of example 22, the ABOA concentrations of the solution ABOA-5-2h have been calculated and shown in the Table 3. At 2 hours, the ABOA concentration of the clear aqueous solution after the filtration was about 98.66% of the ABOA concentration of the clear aqueous solution at 0 hour before the filtration.

TABLE 3

| Solution Number | ABOA Concentration (mg/ml) | Average ABOA Concentration (mg/ml) |
| --- | --- | --- |
| ABOA-5-2h-1 | 0.9894 | 0.9925 |
| ABOA-5-2h-2 | 0.9942 | |
| ABOA-5-2h-3 | 0.9939 | |

At 3 hours, 5 ml of the clear aqueous solution was taken out from the remaining 26 ml of the aqueous solution. The experiments were done for the 5 ml of the clear aqueous solution taken out at 3 hours using the same protocol as for the 5 ml of the clear aqueous solution taken out at 1 hour. Based on the HPLC data and the measurement data of example 22, the ABOA concentrations of the solution ABOA-5-3h have been calculated and shown in the Table 4. At 3 hours, the ABOA concentration of the clear aqueous solution after the filtration was about 98.23% of the ABOA concentration of the clear aqueous solution at 0 hour before the filtration.

TABLE 4

| Solution Number | ABOA Concentration (mg/ml) | Average ABOA Concentration (mg/ml) |
| --- | --- | --- |
| ABOA-5-3h-1 | 0.9899 | 0.9885 |
| ABOA-5-3h-2 | 0.9880 | |
| ABOA-5-3h-3 | 0.9875 | |

At 4 hours, 5 ml of the clear aqueous solution was taken out from the remaining 21 ml of the aqueous solution. The experiments were done for the 5 ml of the clear aqueous solution taken out at 4 hours using the same protocol as for the 5 ml of the clear aqueous solution taken out at 1 hour. Based on the HPLC data and the measurement data of example 22, the ABOA concentrations of the solution ABOA-5-4h have been calculated and shown in the Table 5. At 4 hours, the ABOA concentration of the clear aqueous solution after the filtration was about 98.18% of the ABOA concentration of the clear aqueous solution at 0 hour before the filtration.

TABLE 5

| Solution Number | ABOA Concentration (mg/ml) | Average ABOA Concentration (mg/ml) |
|---|---|---|
| ABOA-5-4h-1 | 0.9879 | 0.9877 |
| ABOA-5-4h-2 | 0.9866 | |
| ABOA-5-4h-3 | 0.9886 | |

At 5 hours, 5 ml of the clear aqueous solution was taken out from the remaining 16 ml of the aqueous solution. The experiments were done for the 5 ml of the clear aqueous solution taken out at 5 hour using the same protocol as for the 5 ml of the clear aqueous solution taken out at 1 hour. Based on the HPLC data and the measurement data of example 22, the ABOA concentrations of the solution ABOA-5-5h have been calculated and shown in the Table 6. At 5 hours, the ABOA concentration of the clear aqueous solution after the filtration was about 98.18% of the ABOA concentration of the clear aqueous solution at 0 hour before the filtration.

TABLE 6

| Solution Number | ABOA Concentration (mg/ml) | Average ABOA Concentration (mg/ml) |
|---|---|---|
| ABOA-5-5h-1 | 0.9872 | 0.9887 |
| ABOA-5-5h-2 | 0.9865 | |
| ABOA-5-5h-3 | 0.9893 | |

At 6 hours, 5 ml of the clear aqueous solution was taken out from the remaining 11 ml of the aqueous solution. The experiments were done for the 5 ml of the clear aqueous solution taken out at 6 hour using the same protocol as for the 5 ml of the clear aqueous solution taken out at 1 hour. Based on the HPLC data and the measurement data of example 22, the ABOA concentrations of the solution ABOA-5-6h have been calculated and shown in the Table 7. At 6 hours, the ABOA concentration of the clear aqueous solution after the filtration was about 98.21% of the ABOA concentration of the clear aqueous solution at 0 hour before the filtration.

TABLE 7

| Solution Number | ABOA Concentration (mg/ml) | Average ABOA Concentration (mg/ml) |
|---|---|---|
| ABOA-5-6h-1 | 0.9856 | 0.9880 |
| ABOA-5-6h-2 | 0.9888 | |
| ABOA-5-6h-3 | 0.9896 | |

Example 24: Composition Comprising ABOA and Human Serum Albumin (HSA)

The ratio by weight of ABOA to HSA prepared was about 1:50.

ABOA (50 mg) was dissolved in methanol (21.4 ml) in a flask to give a clear solution. A solution of HSA (2500 mg, 12.5 ml) (20% human serum albumin solution for infusion (product name: AlbuRx) from CSL Behring) was added into 37.5 ml of water to give a HSA solution (50 ml) in a round bottom flask. The methanol solution of ABOA was added slowly dropwise into the flask of the HSA solution with rapid stirring at 0° C. Upon completion of the addition, a clear solution was obtained. Then, the methanol in the solution was removed under vacuum to give a clear solution. The clear aqueous solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution.

Example 25: Composition Comprising ABOA and Human Serum Albumin (HSA)

The ratio by weight of ABOA to HSA prepared was about 1:40.

ABOA (60 mg) was dissolved in methanol (21.8 ml) in a flask to give a clear solution. A solution of HSA (2400 mg, 12 ml) (20% human serum albumin solution for infusion (product name: AlbuRx) from CSL Behring) was added into 36 ml of water to give a HSA solution (48 ml) in a round bottom flask. The methanol solution of ABOA was added slowly dropwise into the flask of the HSA solution with rapid stirring at 0° C. Upon completion of the addition, a clear solution was obtained. Then, the methanol in the solution was removed under vacuum to give a clear solution. The clear aqueous solution was filtered by a 0.22 micron aqueous phase filter. The resulting clear aqueous solution was lyophilized overnight to give a white solid.

A sample of 100 mg of the lyophilized solid was reconstituted by adding 2 mL water to give a clear solution.

Example 26: Measuring the ABOA Concentrations in the Aqueous Solutions Before and after the Filtration at 0 Hour, and after the Filtration at 1 Hour, 2 Hours, 3 Hours, 4 Hours, 5 Hours, and 6 Hours 1.9 g of the lyophilized solid of the composition comprising ABOA and HSA (the ratio by weight about 1:50) from Example 24 was dissolved in 38 ml of water to give a clear aqueous solution, which was kept at about 25° C. Immediately after the lyophilized solid was dissolved in water, 6 ml of the clear aqueous solution was taken out from the 38 ml solution. Then 1 ml of the solution was taken out from the 6 ml clear aqueous solution to give the solution ABOA-0-0h, and the remaining 5 ml of the solution was filtered by the same 0.22 micron aqueous phase filter at 1 ml at a time to give the solutions ABOA-1-0h, ABOA-2-0h, ABOA-3-0h, ABOA-4-0h, and ABOA-5-0h. To 200 µl of the solutions ABOA-0-0h and ABOA-5-0h were added 800 µl of acetonitrile separately. The mixtures were vortexed for seconds and then centrifuged at 4,000 g for 5 minutes. The supernatants were removed and collected followed by injection on HPLC. The same procedure was repeated 2 more times for each of solutions ABOA-0-0h and ABOA-5-0h. Based on the HPLC data and the measurement data of example 22, the ABOA concentrations of the solutions of ABOA-0-0h, and ABOA-5-0h have been calculated and shown in the Table 8. At 0 hour, the ABOA concentration of the clear aqueous solution after the filtration was about 99.77% of the ABOA concentration of the clear aqueous solution before the filtration.

TABLE 8

| Solution Number | ABOA Concentration (mg/ml) | Average ABOA Concentration (mg/ml) |
| --- | --- | --- |
| ABOA-0-0h-1 | 0.8291 | 0.8299 |
| ABOA-0-0h-2 | 0.8308 | |
| ABOA-0-0h-3 | 0.8298 | |
| ABOA-5-0h-1 | 0.8276 | 0.8280 |
| ABOA-5-0h-2 | 0.8277 | |
| ABOA-5-0h-3 | 0.8287 | |

At 1 hour, 5 ml of the clear aqueous solution was taken out from the remaining 32 ml of the aqueous solution. Then 1 ml of the solution was taken out from the 5 ml clear aqueous solution and filtered by a 0.22 micron aqueous phase filter to give the solution ABOA-1-1h, and the remaining 4 ml of the solution was filtered by the same 0.22 micron aqueous phase filter at 1 ml at a time to give the solutions ABOA-2-1h, ABOA-3-1h, ABOA-4-1h, and ABOA-5-1h. To 200 μl of the solution ABOA-5-1h was added 800 μl of acetonitrile. The mixture was vortexed for seconds and then centrifuged at 4,000 g for 5 minutes. The supernatant was removed and collected followed by injection on HPLC. The same procedure was repeated 2 more times for the solution ABOA-5-1h. Based on the HPLC data and the measurement data of example 22, the ABOA concentrations of the solution ABOA-5-1h have been calculated and shown in the Table 9. At 1 hour, the ABOA concentration of the clear aqueous solution after the filtration was about 99.75% of the ABOA concentration of the clear aqueous solution at 0 hour before the filtration.

TABLE 9

| Solution Number | ABOA Concentration (mg/ml) | Average ABOA Concentration (mg/ml) |
| --- | --- | --- |
| ABOA-5-1h-1 | 0.8273 | 0.8278 |
| ABOA-5-1h-2 | 0.8280 | |
| ABOA-5-1h-3 | 0.8281 | |

At 2 hours, 5 ml of the clear aqueous solution was taken out from the remaining 27 ml of the aqueous solution. The experiments were done for the 5 ml of the clear aqueous solution taken out at 2 hour using the same protocol as for the 5 ml of the clear aqueous solution taken out at 1 hour. Based on the HPLC data and the measurement data of example 22, the ABOA concentrations of the solution ABOA-5-2h have been calculated and shown in the Table 10. At 2 hours, the ABOA concentration of the clear aqueous solution after the filtration was about 99.70% of the ABOA concentration of the clear aqueous solution at 0 hour before the filtration.

TABLE 10

| Solution Number | ABOA Concentration (mg/ml) | Average ABOA Concentration (mg/ml) |
| --- | --- | --- |
| ABOA-5-2h-1 | 0.8288 | 0.8274 |
| ABOA-5-2h-2 | 0.8270 | |
| ABOA-5-2h-3 | 0.8263 | |

At 3 hours, 5 ml of the clear aqueous solution was taken out from the remaining 22 ml of the aqueous solution. The experiments were done for the 5 ml of the clear aqueous solution taken out at 3 hours using the same protocol as for the 5 ml of the clear aqueous solution taken out at 1 hour. Based on the HPLC data and the measurement data of example 22, the ABOA concentrations of the solution ABOA-5-3h have been calculated and shown in the Table 11. At 3 hours, the ABOA concentration of the clear aqueous solution after the filtration was about 99.70% of the ABOA concentration of the clear aqueous solution at 0 hour before the filtration.

TABLE 11

| Solution Number | ABOA Concentration (mg/ml) | Average ABOA Concentration (mg/ml) |
| --- | --- | --- |
| ABOA-5-3h-1 | 0.8253 | 0.8274 |
| ABOA-5-3h-2 | 0.8298 | |
| ABOA-5-3h-3 | 0.8272 | |

At 4 hours, 5 ml of the clear aqueous solution was taken out from the remaining 17 ml of the aqueous solution. The experiments were done for the 5 ml of the clear aqueous solution taken out at 4 hours using the same protocol as for the 5 ml of the clear aqueous solution taken out at 1 hour. Based on the HPLC data and the measurement data of example 22, the ABOA concentrations of the solution ABOA-5-4h have been calculated and shown in the Table 12. At 4 hours, the ABOA concentration of the clear aqueous solution after the filtration was about 99.55% of the ABOA concentration of the clear aqueous solution at 0 hour before the filtration.

TABLE 12

| Solution Number | ABOA Concentration (mg/ml) | Average ABOA Concentration (mg/ml) |
| --- | --- | --- |
| ABOA-5-4h-1 | 0.8279 | 0.8262 |
| ABOA-5-4h-2 | 0.8277 | |
| ABOA-5-4h-3 | 0.8229 | |

At 5 hours, 5 ml of the clear aqueous solution was taken out from the remaining 12 ml of the aqueous solution. The experiments were done for the 5 ml of the clear aqueous solution taken out at 5 hour using the same protocol as for the 5 ml of the clear aqueous solution taken out at 1 hour. Based on the HPLC data and the measurement data of example 22, the ABOA concentrations of the solution ABOA-5-5h have been calculated and shown in the Table 13. At 5 hours, the ABOA concentration of the clear aqueous solution after the filtration was about 99.82% of the ABOA concentration of the clear aqueous solution at 0 hour before the filtration.

TABLE 13

| Solution Number | ABOA Concentration (mg/ml) | Average ABOA Concentration (mg/ml) |
| --- | --- | --- |
| ABOA-5-5h-1 | 0.8276 | 0.8284 |
| ABOA-5-5h-2 | 0.8311 | |
| ABOA-5-5h-3 | 0.8265 | |

At 6 hours, 5 ml of the clear aqueous solution was taken out from the remaining 7 ml of the aqueous solution. The experiments were done for the 5 ml of the clear aqueous solution taken out at 6 hour using the same protocol as for the 5 ml of the clear aqueous solution taken out at 1 hour. Based on the HPLC data and the measurement data of example 22, the ABOA concentrations of the solution ABOA-5-6h have been calculated and shown in the Table 14. At 6 hours, the ABOA concentration of the clear aqueous solution after the filtration was about 99.72% of the ABOA concentration of the clear aqueous solution at 0 hour before the filtration.

TABLE 14

| Solution Number | ABOA Concentration (mg/ml) | Average ABOA Concentration (mg/ml) |
|---|---|---|
| ABOA-5-6h-1 | 0.8298 | 0.8276 |
| ABOA-5-6h-2 | 0.8257 | |
| ABOA-5-6h-3 | 0.8272 | |

Example 27: Measuring the ABOA Concentrations in the Aqueous Solutions Before and after the Filtration at 0 Hour, and after the Filtration at 1 Hour, 2 Hours, 3 Hours, 4 Hours, 5 Hours, 6 Hours, and 24 Hours 2.1 g of the lyophilized solid of the composition comprising ABOA and HSA (the ratio by weight about 1:40) from Example 25 was dissolved in 42 ml of water to give a clear aqueous solution, which was kept at about 25° C. Immediately after the lyophilized solid was dissolved in water, 6 ml of the clear aqueous solution was taken out from the 42 ml solution. Then 1 ml of the solution was taken out from the 6 ml clear aqueous solution to give the solution ABOA-0-0h, and the remaining 5 ml of the solution was filtered by the same 0.22 micron aqueous phase filter at 1 ml at a time to give the solutions ABOA-1-0h, ABOA-2-0h, ABOA-3-0h, ABOA-4-0h, and ABOA-5-0h. To 200 µl of the solutions ABOA-0-0h and ABOA-5-0h were added 800 µl of acetonitrile separately. The mixtures were vortexed for seconds and then centrifuged at 4,000 g for 5 minutes. The supernatants were removed and collected followed by injection on HPLC. The same procedure was repeated 2 more times for each of solutions ABOA-0-0h and ABOA-5-0h. Based on the HPLC data and the measurement data of example 22, the ABOA concentrations of the solutions of ABOA-0-0h, and ABOA-5-0h have been calculated and shown in the Table 15. At 0 hour, the ABOA concentration of the clear aqueous solution after the filtration was about 99.72% of the ABOA concentration of the clear aqueous solution before the filtration.

TABLE 15

| Solution Number | ABOA Concentration (mg/ml) | Average ABOA Concentration (mg/ml) |
|---|---|---|
| ABOA-0-0h-1 | 1.062 | 1.061 |
| ABOA-0-0h-2 | 1.062 | |
| ABOA-0-0h-3 | 1.060 | |
| ABOA-5-0h-1 | 1.060 | 1.058 |
| ABOA-5-0h-2 | 1.058 | |
| ABOA-5-0h-3 | 1.057 | |

At 1 hour, 5 ml of the clear aqueous solution was taken out from the remaining 36 ml of the aqueous solution. Then 1 ml of the solution was taken out from the 5 ml clear aqueous solution and filtered by a 0.22 micron aqueous phase filter to give the solution ABOA-1-1h, and the remaining 4 ml of the solution was filtered by the same 0.22 micron aqueous phase filter at 1 ml at a time to give the solutions ABOA-2-1h, ABOA-3-1h, ABOA-4-1h, and ABOA-5-1h. To 200 µl of the solution ABOA-5-1h was added 800 µl of acetonitrile. The mixture was vortexed for seconds and then centrifuged at 4,000 g for 5 minutes. The supernatant was removed and collected followed by injection on HPLC. The same procedure was repeated 2 more times for the solution ABOA-5-1h. Based on the HPLC data and the measurement data of example 22, the ABOA concentrations of the solution ABOA-5-1h have been calculated and shown in the Table 16. At 1 hour, the ABOA concentration of the clear aqueous solution after the filtration was about 99.72% of the ABOA concentration of the clear aqueous solution at 0 hour before the filtration.

TABLE 16

| Solution Number | ABOA Concentration (mg/ml) | Average ABOA Concentration (mg/ml) |
|---|---|---|
| ABOA-5-1h-1 | 1.060 | 1.058 |
| ABOA-5-1h-2 | 1.057 | |
| ABOA-5-1h-3 | 1.057 | |

At 2 hours, 5 ml of the clear aqueous solution was taken out from the remaining 31 ml of the aqueous solution. The experiments were done for the 5 ml of the clear aqueous solution taken out at 2 hour using the same protocol as for the 5 ml of the clear aqueous solution taken out at 1 hour. Based on the HPLC data and the measurement data of example 22, the ABOA concentrations of the solution ABOA-5-2h have been calculated and shown in the Table 17. At 2 hours, the ABOA concentration of the clear aqueous solution after the filtration was about 99.81% of the ABOA concentration of the clear aqueous solution at 0 hour before the filtration.

TABLE 17

| Solution Number | ABOA Concentration (mg/ml) | Average ABOA Concentration (mg/ml) |
|---|---|---|
| ABOA-5-2h-1 | 1.059 | 1.059 |
| ABOA-5-2h-2 | 1.058 | |
| ABOA-5-2h-3 | 1.059 | |

At 3 hours, 5 ml of the clear aqueous solution was taken out from the remaining 26 ml of the aqueous solution. The experiments were done for the 5 ml of the clear aqueous solution taken out at 3 hours using the same protocol as for the 5 ml of the clear aqueous solution taken out at 1 hour. Based on the HPLC data and the measurement data of example 22, the ABOA concentrations of the solution ABOA-5-3h have been calculated and shown in the Table 18. At 3 hours, the ABOA concentration of the clear aqueous solution after the filtration was about 99.81% of the ABOA concentration of the clear aqueous solution at 0 hour before the filtration.

TABLE 18

| Solution Number | ABOA Concentration (mg/ml) | Average ABOA Concentration (mg/ml) |
|---|---|---|
| ABOA-5-3h-1 | 1.059 | 1.059 |
| ABOA-5-3h-2 | 1.058 | |
| ABOA-5-3h-3 | 1.060 | |

At 4 hours, 5 ml of the clear aqueous solution was taken out from the remaining 21 ml of the aqueous solution. The experiments were done for the 5 ml of the clear aqueous solution taken out at 4 hours using the same protocol as for the 5 ml of the clear aqueous solution taken out at 1 hour. Based on the HPLC data and the measurement data of example 22, the ABOA concentrations of the solution ABOA-5-4h have been calculated and shown in the Table 19. At 4 hours, the ABOA concentration of the clear aqueous solution after the filtration was about 99.81% of the ABOA concentration of the clear aqueous solution at 0 hour before the filtration.

TABLE 19

| Solution Number | ABOA Concentration (mg/ml) | Average ABOA Concentration (mg/ml) |
| --- | --- | --- |
| ABOA-5-4h-1 | 1.061 | 1.059 |
| ABOA-5-4h-2 | 1.059 | |
| ABOA-5-4h-3 | 1.056 | |

At 5 hours, 5 ml of the clear aqueous solution was taken out from the remaining 16 ml of the aqueous solution. The experiments were done for the 5 ml of the clear aqueous solution taken out at 5 hour using the same protocol as for the 5 ml of the clear aqueous solution taken out at 1 hour. Based on the HPLC data and the measurement data of example 22, the ABOA concentrations of the solution ABOA-5-5h have been calculated and shown in the Table 20. At 5 hours, the ABOA concentration of the clear aqueous solution after the filtration was about 99.81% of the ABOA concentration of the clear aqueous solution at 0 hour before the filtration.

TABLE 20

| Solution Number | ABOA Concentration (mg/ml) | Average ABOA Concentration (mg/ml) |
| --- | --- | --- |
| ABOA-5-5h-1 | 1.059 | 1.059 |
| ABOA-5-5h-2 | 1.058 | |
| ABOA-5-5h-3 | 1.060 | |

At 6 hours, 5 ml of the clear aqueous solution was taken out from the remaining 11 ml of the aqueous solution. The experiments were done for the 5 ml of the clear aqueous solution taken out at 6 hour using the same protocol as for the 5 ml of the clear aqueous solution taken out at 1 hour. Based on the HPLC data and the measurement data of example 22, the ABOA concentrations of the solution ABOA-5-6h have been calculated and shown in the Table 21. At 6 hours, the ABOA concentration of the clear aqueous solution after the filtration was about 99.62% of the ABOA concentration of the clear aqueous solution at 0 hour before the filtration.

TABLE 21

| Solution Number | ABOA Concentration (mg/ml) | Average ABOA Concentration (mg/ml) |
| --- | --- | --- |
| ABOA-5-6h-1 | 1.056 | 1.057 |
| ABOA-5-6h-2 | 1.058 | |
| ABOA-5-6h-3 | 1.057 | |

At 24 hours, 5 ml of the clear aqueous solution was taken out from the remaining 6 ml of the aqueous solution. The experiments were done for the 5 ml of the clear aqueous solution taken out at 24 hours using the same protocol as for the 5 ml of the clear aqueous solution taken out at 1 hour. Based on the HPLC data and the measurement data of example 22, the ABOA concentrations of the solution ABOA-5-24h have been calculated and shown in the Table 22. At 24 hours, the ABOA concentration of the clear aqueous solution after the filtration was about 98.21% of the ABOA concentration of the clear aqueous solution at 0 hour before the filtration.

TABLE 22

| Solution Number | ABOA Concentration (mg/ml) | Average ABOA Concentration (mg/ml) |
| --- | --- | --- |
| ABOA-5-24h-1 | 1.043 | 1.042 |
| ABOA-5-24h-2 | 1.041 | |
| ABOA-5-24h-3 | 1.041 | |

Example 28: Measuring pH Value of the Clear Aqueous Solution of Composition Comprising ABOA and Human Serum Albumin (HSA)

250 mg of the lyophilized solid comprising the composition comprising ABOA and HSA (the ratio by weight about 1:50) from Example 24 was dissolved in 10 ml of water to give a clear aqueous solution. The clear aqueous solution was kept at about 25° C. and measured for pH value. The pH value of the clear aqueous solution is 6.18 (3 measurements: 6.17, 6.19, and 6.17).

250 mg of the lyophilized solid comprising the composition comprising ABOA and HSA (the ratio by weight about 1:50) from Example 24 was dissolved in 10 ml of 0.9% saline, which had pH value about 5.41, to give a clear aqueous solution. The clear aqueous solution was kept at about 25° C. and measured for pH value. The pH value of the clear aqueous solution is 6.26 (3 measurements: 6.26, 6.26, and 6.27).

Example 29: Measuring pH Value of the Clear Aqueous Solution of Composition Comprising ABOA and Human Serum Albumin (HSA)

250 mg of the lyophilized solid comprising the composition comprising ABOA and HSA (the ratio by weight about 1:45) from Example 25 was dissolved in 10 ml of water to give a clear aqueous solution. The clear aqueous solution was kept at about 25° C. and measured for pH value. The pH value of the clear aqueous solution is 6.12 (3 measurements: 6.11, 6.13, and 6.12).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A compound, 2-(((3 S,8R,9S,10R,13 S,14S)-10,13-dimethyl-17-(pyridin-3-yl)-2,3,4,7,8,9,10,11,12,13,14,15-dodecahydro-1H-cyclopenta[a]phenanthren-3-yl)oxy)-2-oxoacetic acid (ABOA), or a pharmaceutically acceptable salt thereof, wherein the compound has the structure:

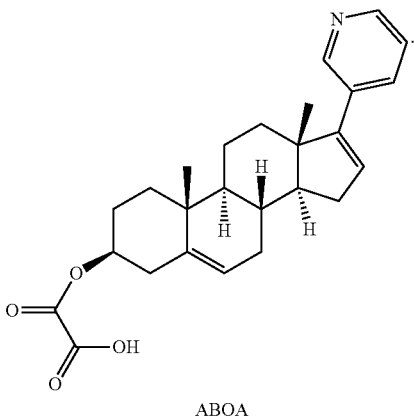

ABOA

2. A pharmaceutical composition comprising ABOA, or a pharmaceutically acceptable salt thereof, and a pharmaceutically acceptable carrier.

3. A composition comprising a non-covalently bound complex comprising ABOA and human serum albumin, wherein the ABOA and the human serum albumin in the composition have a ratio by weight from about 1:1 to about 1:2000.

4. A composition comprising ABOA and human serum albumin, wherein the ABOA and the human serum albumin in the composition have a ratio by weight from about 1:1 to about 1:2000.

5. The composition of claim 4, wherein the ABOA and the human serum albumin in the composition have a ratio by weight from about 1:20 to about 1:600.

6. The composition of claim 4, wherein the ABOA and the human serum albumin in the composition have a ratio by weight of about 1:20, about 1:30, about 1:35, about 1:40, about 1:45, or about 1:50.

7. The composition of claim 3, wherein the composition is a solid formulation.

8. The composition of claim 3, wherein the composition is an aqueous formulation.

9. The composition of claim 8, wherein the aqueous formulation is substantially free of solvent other than water.

10. The composition of claim 8, wherein the aqueous formulation is a clear aqueous solution.

11. The composition of claim 8, wherein the aqueous formulation has pH value from about 5 to about 8.

12. A pharmaceutical composition comprising the composition of claim 3, and a pharmaceutically acceptable carrier.

13. A method of treating a cancer, the method comprising the step of administering to a subject in need thereof a therapeutically effective amount of a pharmaceutical composition of claim 12.

14. The method of claim 13, wherein the cancer is a metastatic castration-resistant prostate cancer.

* * * * *